United States Patent [19]

Garcia et al.

[11] Patent Number: 4,787,398
[45] Date of Patent: * Nov. 29, 1988

[54] GLUCOSE MEDICAL MONITORING SYSTEM

[75] Inventors: Fernando S. Garcia; Hartmut G. Merkert; Paul J. Anderson; David E. Linde; Bertram J. Hudson, all of Eden Prairie, Minn.

[73] Assignee: Garid, Inc., Eden Prairie, Minn.

[ * ] Notice: The portion of the term of this patent subsequent to Jan. 20, 2004 has been disclaimed.

[21] Appl. No.: 889,185

[22] Filed: Jul. 25, 1986

Related U.S. Application Data

[63] Continuation-in-part of Ser. No. 744,539, Jun. 14, 1985, Pat. No. 4,637,403, which is a continuation-in-part of Ser. No. 720,906, Apr. 8, 1985, Pat. No. 4,627,445.

[51] Int. Cl.[4] ............................................. A61B 5/14
[52] U.S. Cl. .................................................. 128/770
[58] Field of Search ................... 128/770, 771, 329 R, 128/314, 315, 763, 636, 637; 356/39–42

[56] References Cited

U.S. PATENT DOCUMENTS

| 3,760,809 | 9/1973 | Campbell | 128/770 X |
| 4,360,016 | 11/1982 | Sarrine | 128/770 X |
| 4,469,110 | 9/1984 | Slam | 122/314 X |
| 4,627,445 | 12/1986 | Garcia et al. | 128/770 |
| 4,635,633 | 1/1987 | Hufnagle | 128/329 R X |

FOREIGN PATENT DOCUMENTS

| 2422260 | 11/1975 | Fed. Rep. of Germany | 128/770 |
| 2834330 | 2/1979 | Fed. Rep. of Germany | 128/770 |

Primary Examiner—Edward M. Coven
Attorney, Agent, or Firm—Hugh D. Jaeger

[57] ABSTRACT

Hand-held shirt-pocket portable glucose medical monitoring system for checking measurement of blood glucose or other body qualities. The system includes a disposable diagnostic reagent-lancet unit which carries a chemcial reagent strip of blood reacting chemistry. The system includes a housing structure having a visual LCD readout, a microprocessor, and photosensing circuitry which measures the change of color of the blood reacting chemistry of the disposable unit. The housing also includes a spring arrangement for actuating a lancet into the skin for sampling and transporting blood from a finger to a chemical reagent. The disposable unit includes medical and fluid configurations for transporting of the blood to the reagent strip. The system inlcudes verification and calibration sequences for the electronics, the chemistry of an unused disposable unit, the presence of a blood sample, and multiple readings to an average result. The system also provides for storing a plurality of readings.

26 Claims, 23 Drawing Sheets

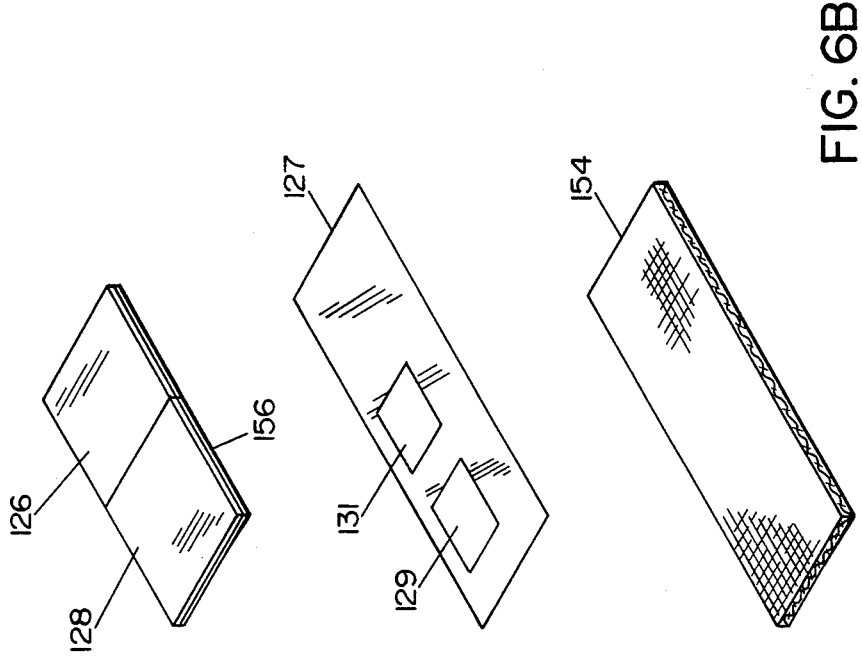

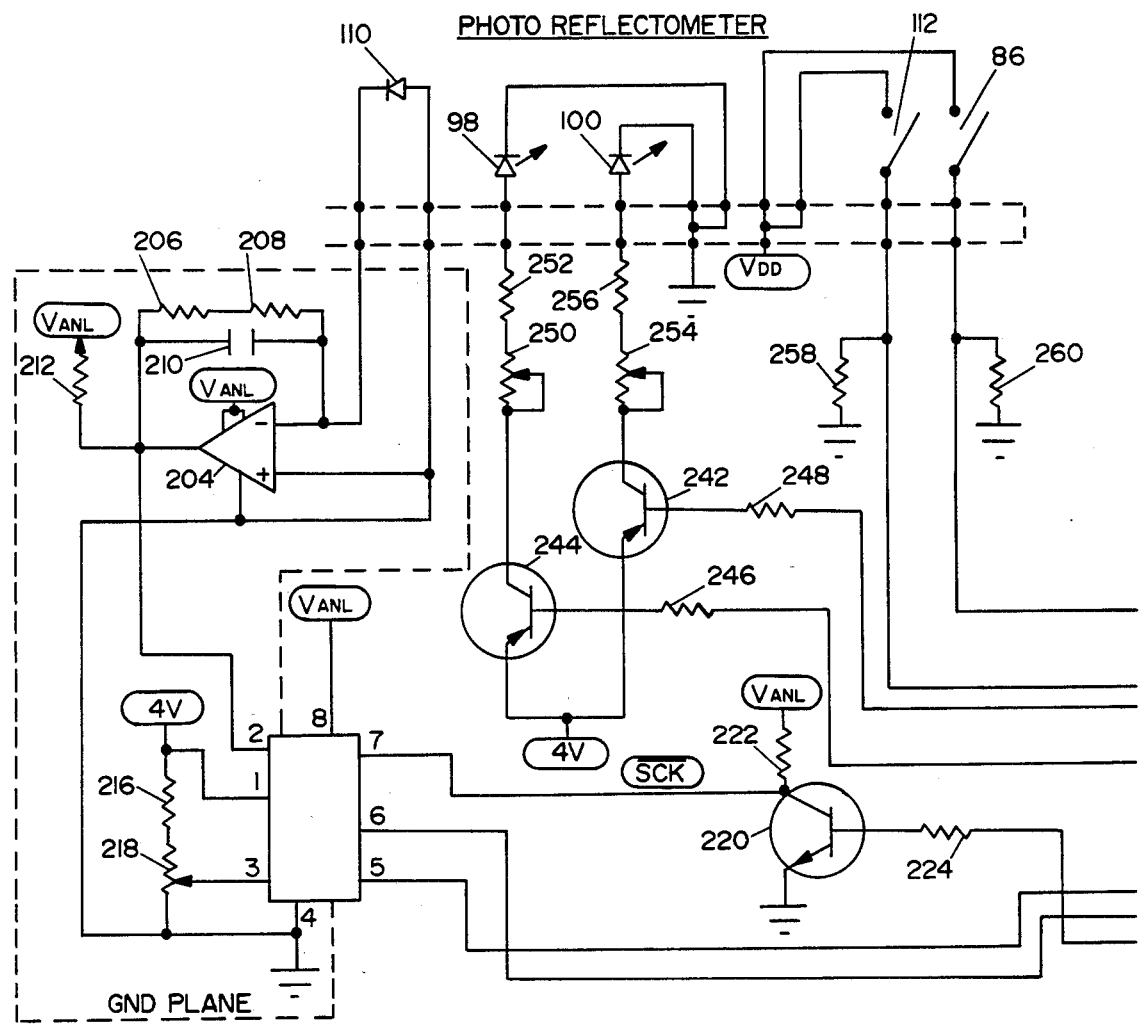
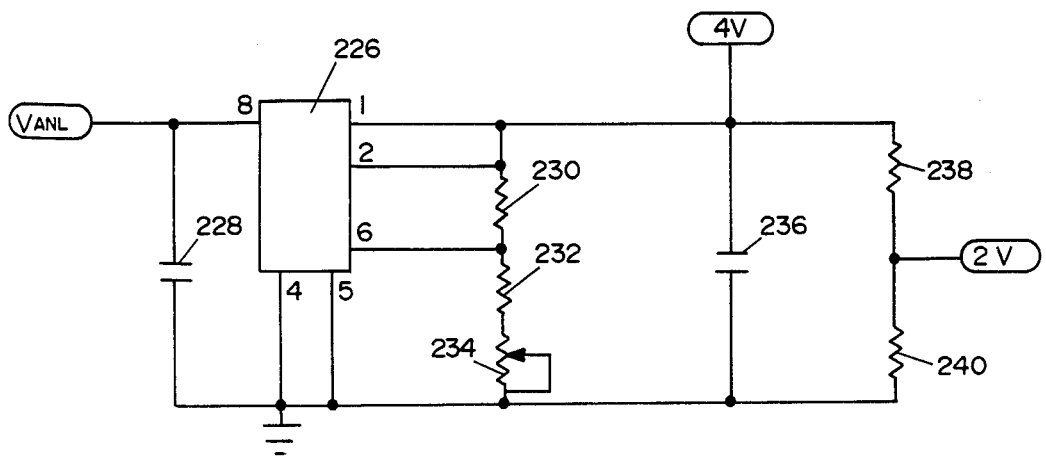
FIG. 8A

FIG. 11A

TABLE 1 - 14 SYSTEM PROCEDURE STEPS

| STEP | EVENT USER VIEWPOINT | DESIGN VIEWPOINT | LIQUID CRYSTAL DISPLAY | DURATION | AUDIBLE BEEPS | NOTES |
|---|---|---|---|---|---|---|
| 1 | DUST COVER IN PLACE | NONE | NONE | N/A | NONE | IN ORDER TO PERFORM ELECTRONIC CHECK |
| 2 | PUSH HAMMER MECHANISM UP | COCK HAMMER SPRING | NONE | N/A | NONE | |
|  |  | CLOSE 86 CONTACTS | NONE | N/A | NONE | |
|  |  | ENTER SYSTEM MODE APPLY REST OF POWER SAVINGS | NONE | N/A | NONE | |
|  |  | BATTERY CHECK:  A  OK |  | NOTE M | NONE | |
|  |  | B  LOW |  | UNTIL RETURNING TO CLOCK MODE | NONE | |
|  |  | C  NOT OK | EEE | NOTE D | 3 | NOTE B |
|  |  | PERFORM ELECTRONIC CHECK:  OK | - - - | NOTE C | 1 | NOTE B |
|  |  | NOT OK | EEE 1 | NOTE D | 3 | NOTE B |
| 3 | OPEN DUST COVER | NONE | - - - | NOTE C | NONE | NOTES A, B |
| 4 | INSERT LANCET UNIT | CLOSE 112 CONTACTS | - - - | NOTE C | NONE | NOTES A, B |
|  |  | CHEMISTRY AND LOT TO LOT CHECK:  OK |  | NOTE C | 1 | NOTES A, B & L |
|  |  | NOT OK CHEMISTRY NOT OK | EEE 3 | NOTE D | 3 | NOTE B |
|  |  | 112 CONTACTS OPEN | EEE 2 | NOTE D | 3 | NOTES B & K |
|  |  | 112 CONTACTS OPEN | EEE 5 | NOTE J | 3 | NOTE J |
| 5 | HOLD SYSTEM IN HAND (PROPERLY) | NONE | - - - | NOTE C | NONE | NOTES B & J |

FIG. 11B

| STEP | EVENT USER VIEWPOINT | DESIGN VIEWPOINT | LIQUID CRYSTAL DISPLAY | DURATION | AUDIBLE BEEPS | NOTES |
|---|---|---|---|---|---|---|
| 6 | CENTER SYSTEM OVER PUNCTURE SITE | NONE | --- | NOTE C | NONE | NOTES B & J |
| 7 | ACTIVATE LANCET | 60 SEC INTERNAL COUNTDOWN BEGINS | --- | NOTE F | NONE | NOTES B & J |
| 8 | MASSAGE FINGER TO OBTAIN BLOOD | NONE | --- | NOTE F | NONE | NOTES B & J |
| 9 | TOUCH BLOOD TO WICK | NONE | --- | NOTE F | NONE | NOTES B & J |
| 10 | LISTEN FOR SYSTEM TO BEEP (TIME INTERNAL WHILE SYSTEM IS SCANNING FOR COLOR CHANGE | WICK TRANSPORT SAMPLE TO REAGENT | --- | NOTE G | NONE | NOTE B |
|  |  | ELECTRONIC MONITOR FOR CHEMISTRY OK |  | NOTE G | 1 | NOTES B, E, H & J |
|  |  | REACTION NOT OK INITIATED AT STEP 7) | EEE 4 | NOTE D | 3 | NOTES B, I & J |
| 11 | REMOVE SYSTEM FROM FINGER | COUNTDOWN FROM 60 TO 0 SECONDS | 60, 59, 58...0 | NOTE G | NONE | NOTES B, J & K |
| 12 | READ GLUCOSE LEVEL OFF LCD | TEST RESULTS EQUAL TO OR WITHIN RANGE DISPLAYED | ACTUAL VALUE | MINIMUM: REMOVAL OF LANCET UNIT | 1 | NOTE B |
|  |  | ABOVE RANGE | "HHH" | MAXIMUM: UNTIL LANCET UNIT IS REMOVED | 1 | NOTES B & M |
|  |  | BELOW RANGE | "LLL" |  |  | NOTES B & M |
| 13 | REMOVE LANCET UNIT |  |  |  | NONE | NOTE B LIFO |
| 14 | REPLACE DUST COVER | NONE | SAME AS STEP 13 OR NONE | SAME AS STEP 13 OR N/A | NONE | NOTE B LIFO |

TABLE 2

ERROR MESSAGES
(REFER TO TROUBLESHOOTING)

1.          LOW BATTERY

2. EEE    DEAD BATTERY

3. EEE 1   ERROR IN DUST COVER READING (ELECTRONIC CALIBRATION)

4. EEE 2   ERROR IN LANCET UNIT ENGAGEMENT (WHILE SENSING CIRCUITS ACTIVE)

5. EEE 3   ERROR IN LANCET UNIT CALIBRATION (BAD CHEMISTRY)

6. EEE 4   VALID SAMPLE NOT OBTAINED IN 60 SECONDS

7. EEE 5   ERROR IN LANCET UNIT ENGAGEMENT (WHILE SENSING CIRCUITS INACTIVE)

8. HOT    TEMPERATURE OF LANCET UNIT IS ABOVE NORMAL OPERATING CONDITIONS. (35 C OR 95 F)

9. CLD    TEMPERATURE OF LANCET UNIT IS BELOW NORMAL OPERATING CONDITIONS. (15 C OR 59 F)

FIG. 11C

NOTES

NOTE A: VISUAL DISPLAY NOT INDUCED BY THE EVENT. IT IS CARRIED OVER FROM A PREVIOUS SUCCESSFUL EVENT.

NOTE B: BATTERY SYMBOL MAY ALSO BE ON LCD IF BATTERY WAS LOW FROM EVENT 2(B).

NOTE C: IF NO FURTHER USER ACTIONS ARE TAKEN WITHIN 3 MINUTES, EEE2 IS DISPLAYED UNTIL LANCE HAMMER IS FIRED.

NOTE D: DISPLAY DURATION UNTIL HAMMER IS FIRED. IF ERROR OCCURRED WITH HAMMER FIRED, DISPLAY DURATION IS 3 MINUTES, OR UNTIL LANCE IS ARMED AGAIN.

NOTE E: VISUAL DISPLAY FLASHING.

NOTE F: VISUAL DISPLAY FOR 60 SECONDS OR UNTIL ADEQUATE SAMPLE OBTAINED, WHICHEVER OCCURS FIRST.

NOTE G: VISUAL DISPLAY UNTIL CHEMICAL REACTION IS COMPLETED.

NOTE H: ONCE THE SENSING CIRCUITS DETECT A COLOR CHANGE IN THE CHEMISTRY, THEN IF THE SENSING CIRCUITS ALSO DETECT A COLOR CHANGE IN THE LOT/LOT AREA WITHIN TEN (10) SECONDS THEN A SUCCESSFUL SAMPLE HAS BEEN OBTAINED.

NOTE I: EEE 4 WILL OCCUR IF THE REQUIREMENTS OF NOTE H DID NOT OCCUR WITHIN THIRTY (30) SECONDS OR THE SENSING CIRCUITS DID NOT DETECT A COLOR CHANGE IN THE CHEMISTRY (AT ALL).

NOTE J: ONCE THE LANCET UNIT IS INSERTED (24 CONTACTS CLOSED) EEE 5 CAN OCCUR AS DEFINED IN PARAGRAGH 2.2.11.B.

NOTE K: EEE 2 CAN DISPLAY AS DEFINED IN TABLE 2.

NOTE L: WAIT FOR TWO SECONDS FOR LANCET UNIT SETTLING BEFORE CHECKING POINT.

NOTE M: THE READINGS "HHH" OR "LLL" WILL BE STORED IN MEMORY.

NOTE N: BATTERY CHECK IS PERFORMED EVERY A/D READING.

FIG. 11D

GLUCOSE MEDICAL MONITORING SYSTEM

CROSS REFERENCES TO CO-PENDING APPLICATIONS

This application is a continuation-in-part of Ser. No. 744,539, now U.S. Pat. No. 4,637,403, filed June 14, 1985, which is a continuation-in-part of Ser. No. 720,906, filed Apr. 8, 1985, now U.S. Pat. No. 4,627,445.

BACKGROUND OF THE INVENTION

1. Field of the Invention

The present invention pertains to glucose medical monitoring system for sampling and analyzing blood or any components of the blood for specific readings as to qualities of the blood. One specific use of the present invention is for sensing the accumulation of blood glucose for diabetics. The system is a portable, pocket-size, battery operated, diagnostic system for detection monitoring and measurement of blood glucose qualities or of other predetermined qualities.

2. Description of the Prior Art

Prior art blood glucose devices have operated on the principle of taking blood from an individual by a variety of methods, such as by needle or lance. An individual then had to coat a paper strip carrying chemistry with the blood, time the chemical reaction for about 60 seconds, wipe or remove the blood sample from the strip, and insert the blood-coated strip into a blood glucose meter or visual comparison against a color standard.

There are numerous blood glucose meters in the marketplace, but the instruments consume physical space and are not pocketable. The instruments usually have to be carried in a large handbag, or an individual's briefcase, or left at home such as in the bathroom or the bedroom on a counter or table.

Further, the prior art medical apparatuses for sensing blood glucose required that an individual have separately available a needle or lance for extracting blood from the individual, strips carrying blood chemistry for creating a chemical reaction with respect to the blood glucose and changing color, and a blood glucose meter for reading the change in color indicating the blood glucose level. The level of blood glucose, when measured by a glucometer, is read from a strip carrying the blood chemistry through the well-known process of reflectometers based on the principle of glucose oxidation.

Monitor/reagent strip systems that are now available on the market have multiple sequential steps that the patient must follow at exact time intervals. Each step is subject to error by the patient. As in most monitors, it is the patient's responsibility to periodically calibrate the monitor against known color standards; validate the efficacy of the reagent strips and technique by immersing the strips in a control solution of known glucose content; and, then comparing the color change visually against the color standard or by using a calibrated monitor. These types of prior art systems are subject of course to human error.

In the prior art, the procedure for obtaining accurate results from the time a drop of blood is placed on a reagent strip pad to the time the pad color change may be read in the glucose monitor is as now described. The patient must stick himself/herself with a lancet. A drop of blood must be milked or squeezed to the surface of the skin. The drop of blood must then be carefully placed on the reagent pad, making sure to cover the pad completely and that the pad is never be touched by the finger of the patient to prevent contamination. Once the sample has been applied to the surface of the reagent pad, the patient must press a timer on the monitor. At the end of the timing, the patient must wipe, blot or wash the strip off, using a careful technique. And for most strips, the patient must place the reacted reagent strip into the monitor, and press a test button or close a hatch to obtain results. Prior art commercially available comparable reagent strips or monitors require operator intervention in a prescribed sequence at exact time intervals. The prior art monitors are subject to operator error, sequence errors, timing errors, and technique errors. The prior art reagent strips are also subject to contamination which may affect accuracy of measurement.

The present invention overcomes the disadvantages of the prior art by providing a hand-held pocketable glucose medical monitoring system which includes an attachable disposable lancet reagent unit carrying a chemical reagent chemistry for extracting blood from an individual, transporting the blood to the blood sensing reagent, resulting in a readout of a level of the blood glucose. The system includes a microprocessor which is software controlled by an internal program. The microprocessor controls all (timing) functions, including timing, thereby eliminating human error.

SUMMARY OF THE INVENTION

One general purpose of the present invention is a portable, shirt-pocket-size, battery-operated diagnostic system for use by health professionals and/or lay patients for the detection and measurement of certain selected chemical agents or substances for the purpose of diagnosis and/or treatment of disease. The system application is not restricted to use with human beings. The system may also be extended to veterinary medicine animals, and can also have uses in the agricultural field, such as measurement of glucose in grapes in the wine industry. One such application is for insulin dependent and non-insulin dependent diabetics for the measurement of glucose in serum, plasma, and/or whole blood. The particular quantity to be measured is glucose through the principles of either reflectance, adsorption or potentiometric measurement by electronic circuitry although other quantites can be measured.

Another purpose of the present invention is to provide a hand-held pocketable medical (system or) measurement system including the engaging of a disposable diagnostic reagent lancet unit carrying the blood sensing reagent for sensing readings of the blood, such as blood glucose level. The medical system is cost effective and simple to operate by an individual. The reading, such as an individual's glucose level, is displayed on an LCD display on the side of a housing of the medical system which approximates the size of an ordinary highlighter which can be carried in an individual's shirt pocket. The disposable diagnostic reagent lancet packages can be carried in a corresponding hollow member carrying a plurality of disposable units for use as needed. The housing structure resembling a highlighter contains the hand-held pocketable medical system. A like housing structure resembling a highlighter carriers the extra supply of disposable units. The design of the present invention provides for the utmost peace of mind for the individual.

According to one embodiment of the present invention, there is provided a hand-held pocketable medical system including an electromechanical structure for actuating a lancet in a disposable diagnostic reagent or lancet disposable package which engages onto the system. The disposable package enables a blood sample inside a finger or on the finger surface to be transferred to the blood reagent chemistry. The electromechanical structure includes a spring actuated configuration for movement of a hammer mechanism. The disposable diagnostic reagent lancet unit frictionally engages and slides onto the bottom of the hand-held pocketable medical system, and is easily releasable and disposable after a single use.

The hand-held medical system includes light tight compartment with photosensing electronics connected to a microprocessor for analyzing the properties of the blood sensing chemistry in the disposable unit, and for displaying a readout and storing previous readouts. The electronics includes verification sequences for verifying operability of the electronics including annunciating of a low battery condition, for verifying the condition of an unused disposable unit, for verifying the presence of a blood sample and for subsequently providing multiple readings to provide for an averaging of results.

According to other embodiments of the present invention, there is provided a disposable diagnostic reagent lancet unit with a transporting action where a wick serves as the transport structure for the blood.

One significant aspect and feature of the present invention is a hand-held pocketable diagnostic medical monitoring system which is utilized for extracting a blood sample from the body, subjecting the sample to chemical analysis, and visually displaying the numerical results to the individual. A disposable diagnostic reagent lancet unit carries the blood sensing chemistry consisting of a reagent strip as well as a lancet for either delivering blood to the reagent or for causing the reagent to be delivered to the blood. Additional disposable units can be carried in a corresponding structure similar to that of the medical system.

Another significant aspect and feature of the present invention is a housing like structure which is electromechanical, and where a button is pushed actuating a hammer in the housing structure against the lancet through spring driven structure. A hammer return spring returns the hammer back to an original rest position. When the hammer returns to the original rest position, the modules of elasticity of the living spring lancet removes the sharp point of the lancet from the finger.

A further significant aspect and feature of the present invention is a hand-held pocketable diagnostic medical monitoring system which will provide blood glucose readings where the disposable diagnostic reagent lancet package carries glucose-oxidase or like chemical reagent. Once the reagent undergoes a colorimetric, potentiometric, or absorption action proportional to the blood glucose concentration, electronics through the reflectance colorimeter provide for subsequent processing of the photosensing of the blood chemistry for displaying of the results on an LCD display.

Another significant aspect and feature of the present invention is a system which utilizes a slidable disposable diagnostic reagent lancet unit. The unit carries a lancet and a transport mechanism for transporting a fluid or fluid to the reagent strip.

Having thus described embodiments of the present invention, it is principal objects hereof to provide a pocketable diagnostic medical monitoring system, including disposable diagnostic reagent lancet package which carries blood sensing reagent and which engages onto the system for providing a subsequent readout on a visual display of the system of a quality of the blood. The medical system can be broadly extended to a system for measurement of a quantity of a substance in a particular fluid or material, and is not to be construed as strictly limited to medical applications, as the system can be used in industry, agricultural, or even veterinary environments.

One object of the present invention is to provide a hand-held pocketable diagnostic medical monitoring system with a disposable diagnostic reagent lancet unit which engages onto the electromechanical assembly of the medical system. A separate like hollow member can carry extra disposable diagnostic units. The disposable diagnostic units carry blood sensing reagent for sensing components of the blood for qualities such as glucose level. Other qualities of fluid can be measured such as urea, nitrogen, hemoglobin, alcohol, protein or other qualities of the blood with appropriate reagent.

Another object of the present invention is an electromechanical assembly which contains the microprocessor including the software, mechanical and electromechanical apparatus, batteries, and related circuitry that causes the electrical and electromechanical functional operation. The diagnostic unit is a disposable unit containing the lancet for obtaining a blood sample, typically from a person's finger or toe, and a chemical reagent that reacts with the presence of blood as a function of the amount of glucose present in blood. The chemical reagent is sealed inside the unit housing minimizing the effects of contamination from fingers, moisture, and light, thus improving accuracy and precision of measurement by stabilizing the oxidation reduction or chemical reaction of the reagent prior to use. The sensor in the assembly detects and measures via absorption, potentiometric, or reflectance analysis the amount of glucose present. This analog data is converted to a digital readout display quantifying glucose in milligrams per deciliter (mg/dl) or MMOL/L.

An additional object of the present invention is a self-contained automatic medical monitoring system. All operations and performance of the system are performed automatically, mechanically and electronically in proper sequences. Accuracy and precision of the measurement is enhanced because errors due to operator interpretation, operator technique, and timing of events, are removed from operator control because of microprocessor based system operation.

Still another object of the present invention is a medical diagnostic system which is software controlled and software intelligent. The system is self-calibrating through control commands by the software.

DESCRIPTION OF THE PREFERRED EMBODIMENTS

Other objects and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 6B illustrates an exploded view of the reagent pad and associated components;

FIGS. 8A and 8B illustrate an electrical circuit schematic diagram of the glucose medical monitoring system;

Figure 12A:
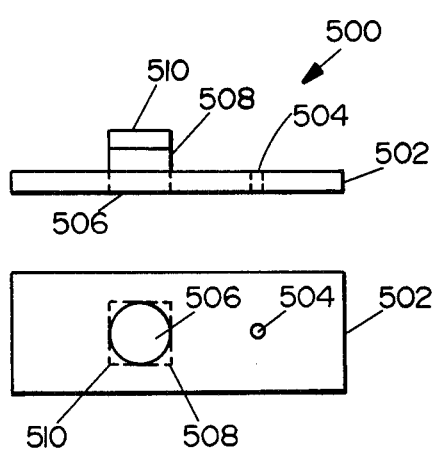
Figure 12B:
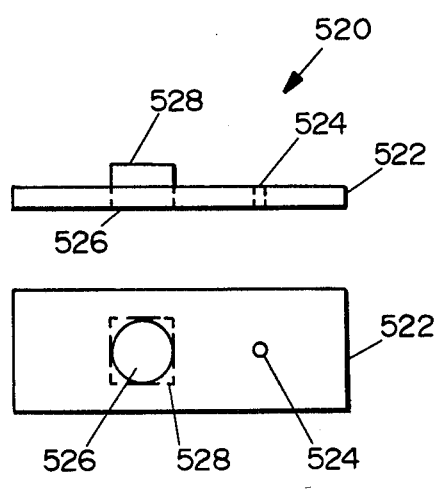
Figures 13A, 13B:
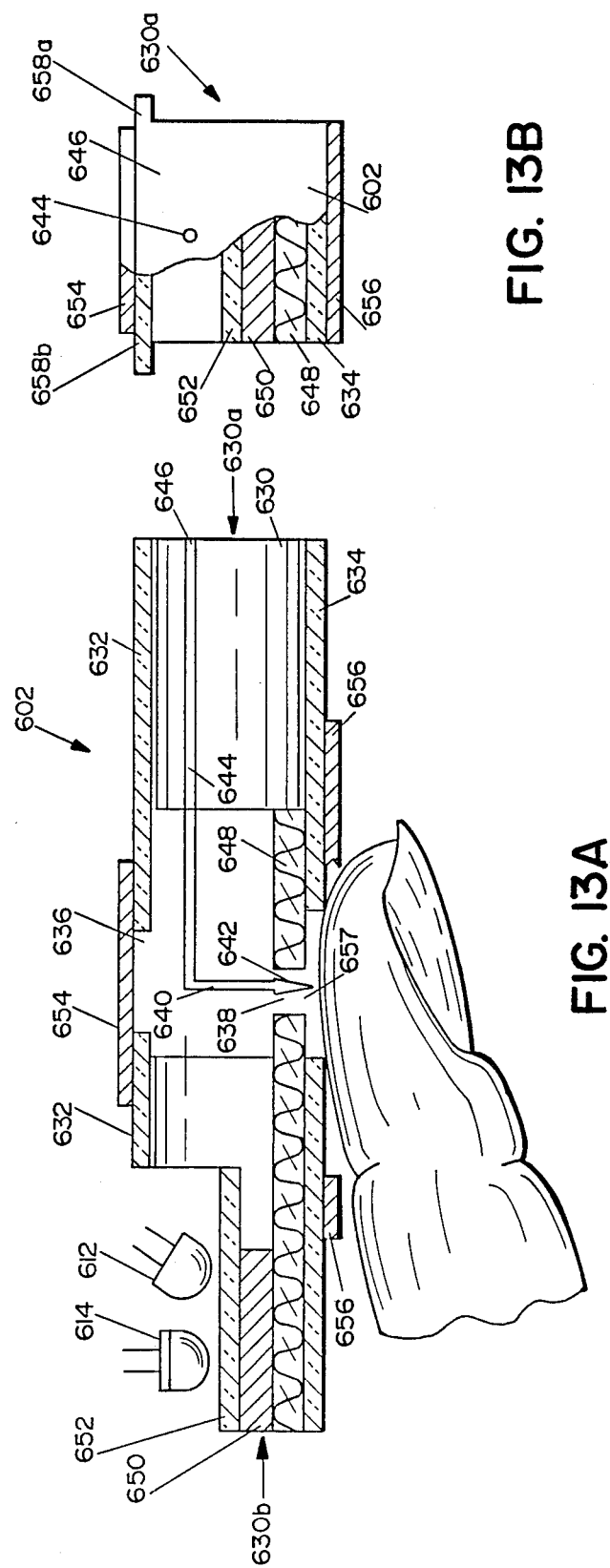

FIGS. 11A-11D describe the procedural operation and internal steps of the flow chart;

FIGS. 12A and 12B illustrate alternative embodiments of disposable diagnostic reagent lancet units, and;

FIGS. 13A and 13B illustrate an alternative embodiment of another disposable diagnostic reagent lancet unit.

DESCRIPTION OF THE PREFERRED EMBODIMENTS

Figure 1:
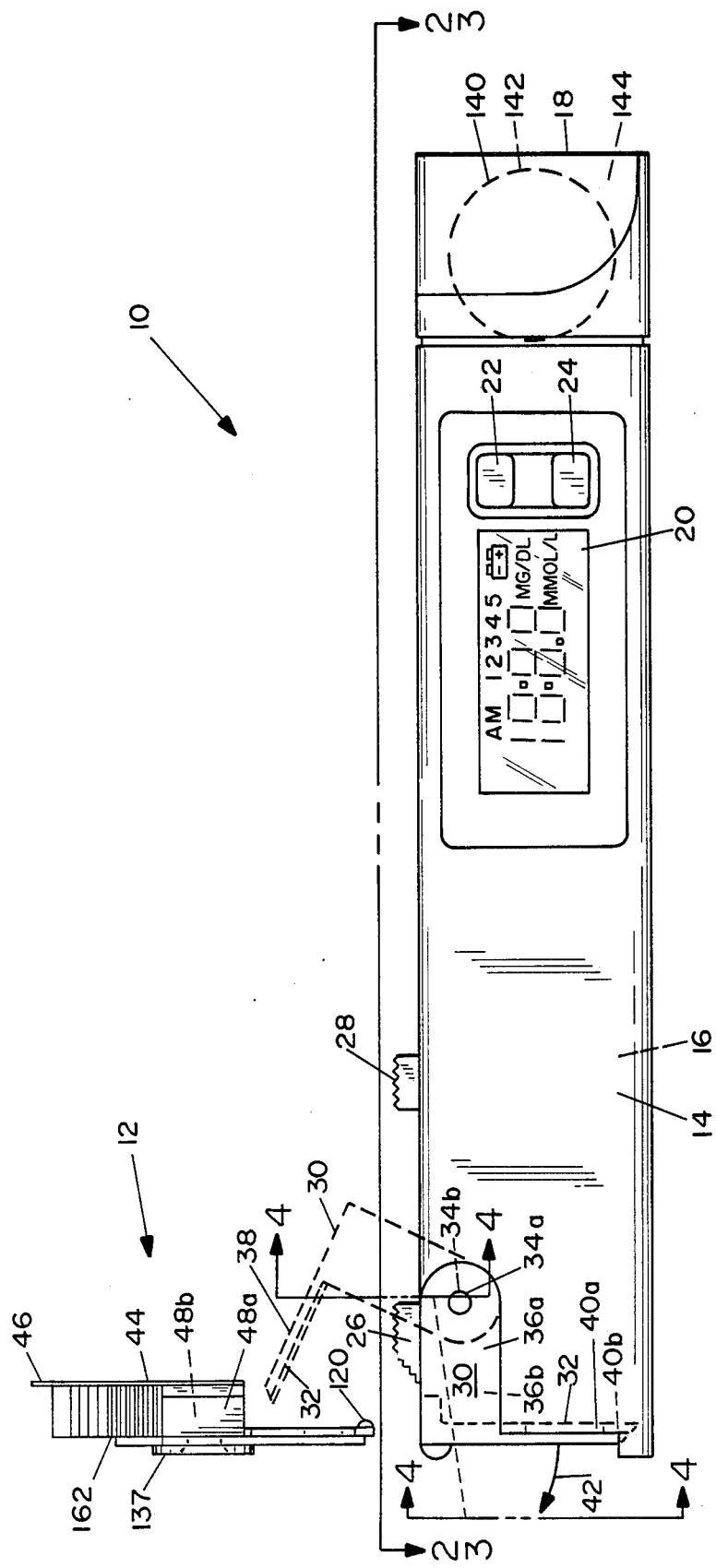
FIG. 1 illustrates a plan view of an embodiment of a glucose medical monitoring system.

FIG. 1 illustrates a plan view of a portable pocketable glucose medical monitoring system 10 including a disposable diagnostic reagent lancet unit 12 as illustrated and later described in particular detail in FIG. 6. Externally visible components of the system 10 include front and back housings 14 and 16 respectively which enclose the electromechanical structure as now described and a battery retainer cap 18. An LCD or like vusual readout 20 displays the glucose levels, time, battery condition, stored values in memory, and other mode operational displays as later described in detail. Time set buttons 22 and 24 position adjacent to the LCD readout 20. A cocking lever 26 and a hammer release button 28 locate on the top side of the glucose medical monitoring system 10 for subsequent cocking and releasing of the spring mechanism as later described in detail in FIG. 3. A flush rotatable protective dust cover 30 including an interior mounted calibration strip 32 rotates on pivot pins 34a–34b, and seats inside conforming recesses 36a–36b on the front housing 14 and the back housing 16 respectively. The end portion 38 of the dust cover 30 fit into recesses 40a and 40b on the ends of the housings 14 and 16. The dust cover 30 is rotated as shown by arrow 42 to a position as indicated in the figure by dashed lines, allowing for insertion of the disposable diagnostic reagent lancet unit 12 and as poised for insertion in this figure, and as also illustrated in the inserted position in FIG. 3. A polyester sterility barrier 44 as illustrated in FIG. 6, with pull tab 46 affixes to the unit 12, and is removed prior to the unit 12 insertion. Engagement slots 48a and 48b of unit 12 align within the system 10 for proper positioning of the unit 12 within the system 10.

Figure 2:
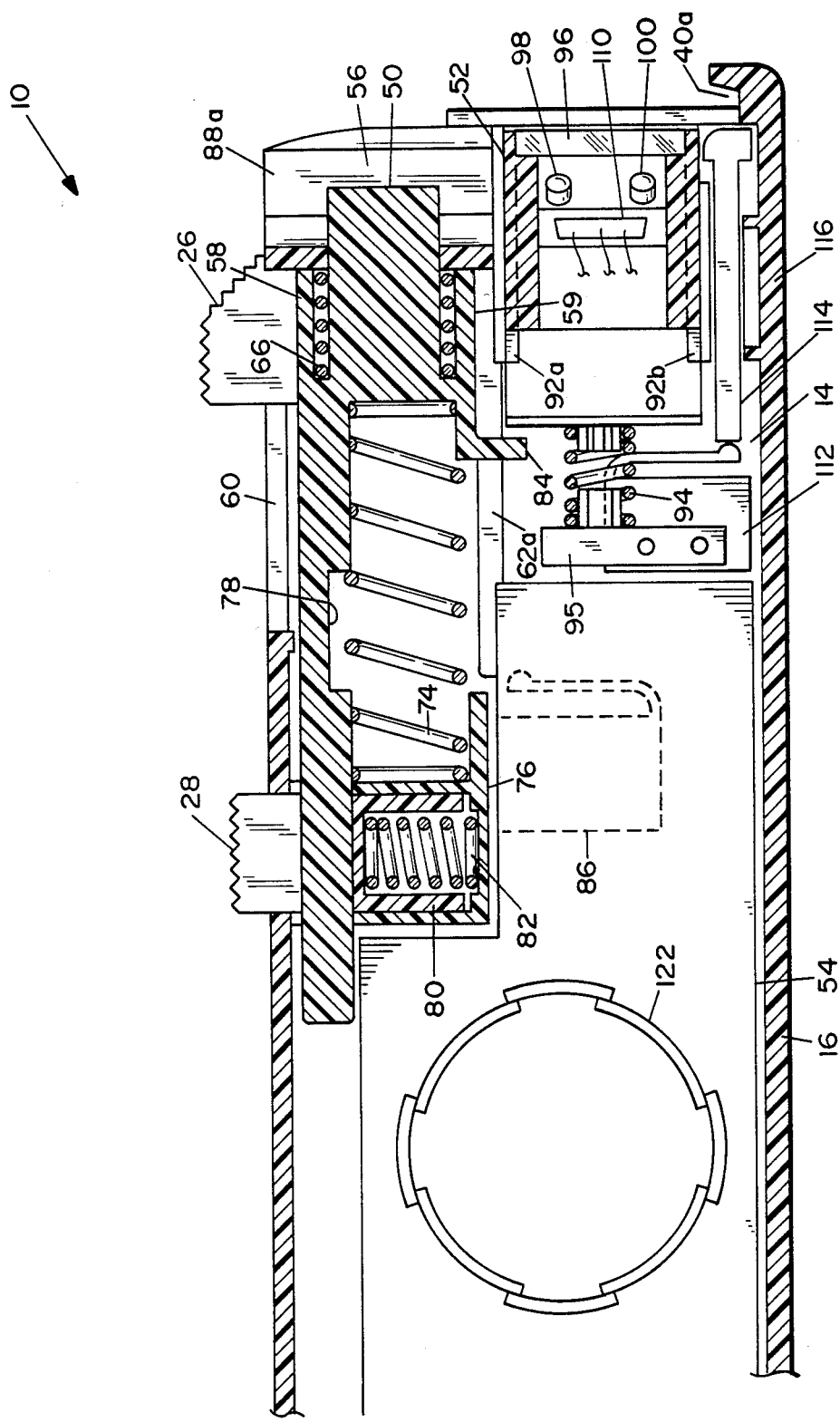
FIG. 2 illustrates a sectional view of FIG. 1 along lines 2—2, as viewed from the back side of FIG. 1.
Figure 4:
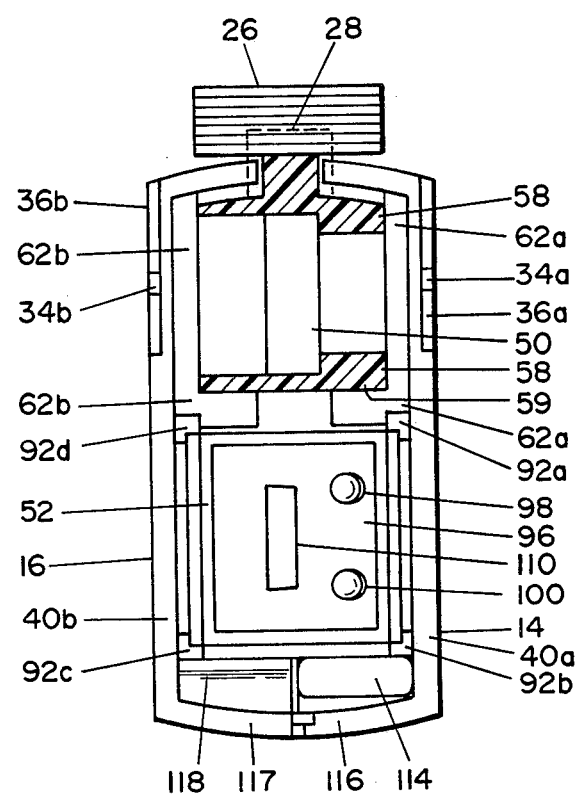
FIG. 4 illustrates an end view in partial cross section taken along line 4—4 of FIG. 1.

FIG. 2 illustrates a sectional view of FIG. 1 along lines 2—2 as viewed from the back side of the front housing 14. A hammer 50 integrated to hammer casing 58 connects on to a cocking lever 26 as an integral member. An integral member cocking lever 26, of the hammer casing 58 slides longitudinally in an upper slot 60. The hammer casing bottom 59 slides longitudinally in the front hammer track member 62a and the back hammer track member 62a as also illustrated in FIG. 4. Both track members 62a and 62b are molded integrally into the respective front and back housings 14 and 16, and extend vertically and horizontally as also illustrated in FIG. 4.

The rectangularly shaped hammer 50 is positioned and retained partially within the hammer casing 58. A first spring 66 positions about the hammer 50 for returning the integral member to a neutral position. A second spring 74 seats between a surface adjacent to the hammer casing 58 and dual spring seat member 76 for powering of the hammer 50. A first catch 78 is integral and positions at the interior portion of the hammer casing 58 for subsequent engagement with second catch 80 of the spring lever hammer release button 28. Second catch 80 and a catch spring 82 position with the dual spring seat member 76 for subsequent engagement of second catch 80 with the first catch 78 when the cocking lever 26 is activated. A switch actuator tab 84 positions at the bottom of the hammer casing 58 for electromechanical actuation of the switch 86. The action of the switch 86 is discussed later in detail in FIG. 7, and FIGS. 8A and 8B.

Figure 3:
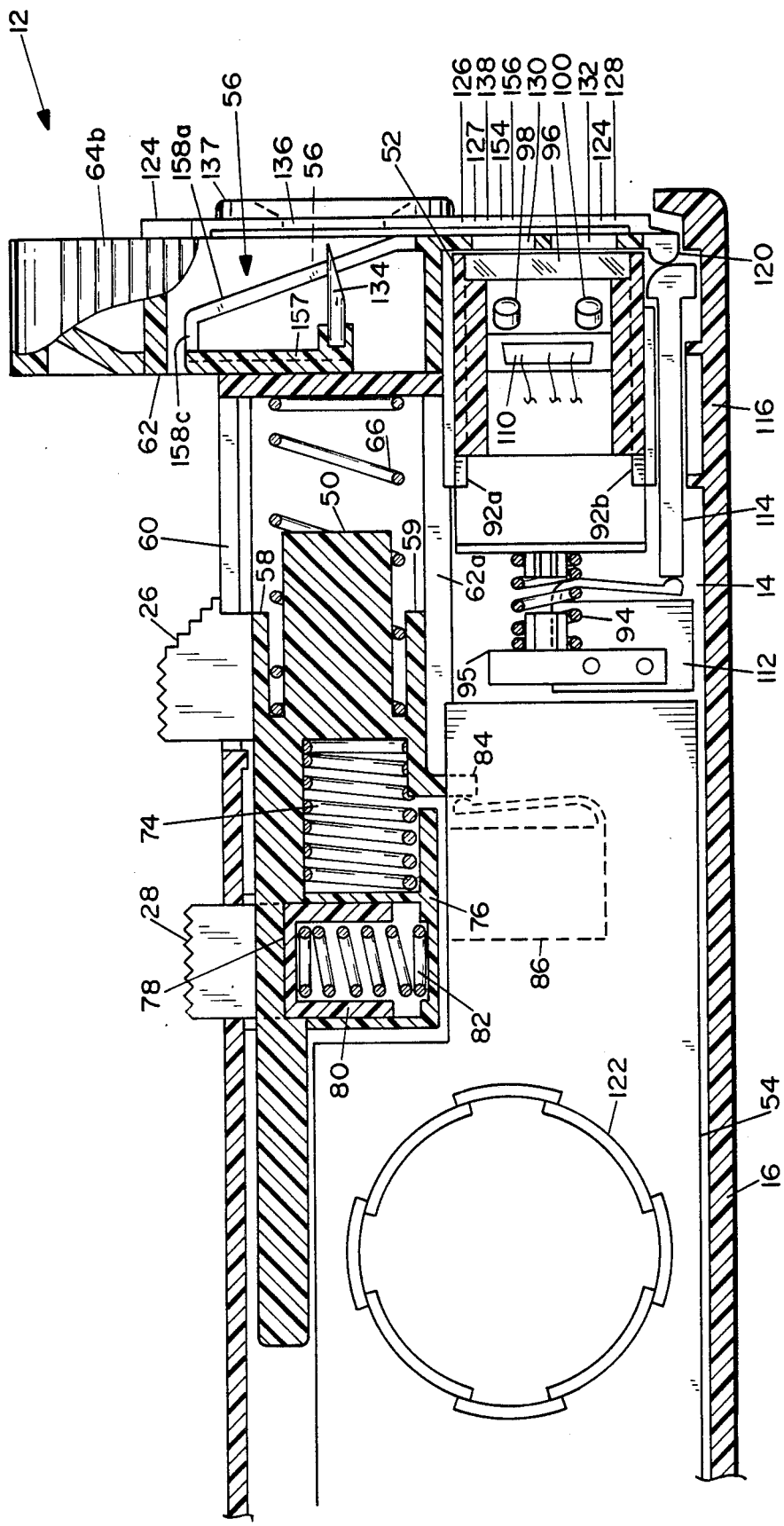
FIG. 3 illustrates a view taken along line 3—3 of FIG. 1 with a disposable diagnostic reagent-lancet unit positioned in the glucose medical monitoring system.

A diagnostic disposable reagent-lancet unit engagement area 56 positions in front of and outwardly from the area of the hammer 50. Engagement slots 48a and 48b align the disposable diagnostic reagent-lancet unit 12 by positioning over engagement members 88a and 88b respectively. FIG. 3 illustrates the disposable diagnostic reagent-lancet unit 12 engaged within engagement area 56 as later described in detail.

A floating optics head 52, whose purpose is to determine the color of blood samples and to calibrate the medical system, positions beneath the engagement area 56 at the lower end position of the housing. The head 52 rides longitudinally within four channel members 92a–92d in a light tight-box environment. The head 52 is spring loaded outwardly for close engagement to the inner surfaces of the disposable diagnostic reagent-lancet 12 by a spring member 94 which seats against and within a spring retainer 95. A lens 96 mounts internally within the outer edges of the square shaped head 52. The square shaped head 52 is constructed of a dense, dark, light resistant material to inhibit and stop stray light through the lens edge from influencing readings taken by the glucose medical monitoring system electronic circuitry on the circuit board 54. Reagent LED 98, LOT/LOT LED 100 and photo diode 110, for measurement of the LOT/LOT comparison and the reagent strip mounts within the floating optics head 52. Reagent LED 98 and LOT/LOT LED 100 cant inwardly toward the center line between the diode 110 and LED 98, and LOT/LOT LED 100. Photodiode 110 cants 30 degrees by way of example inwardly toward the center line between the LEDS 98 and 100, and the photo diode 110. Canting of the photo diode 110 and LED'S 98 and 100 provides for maximum readability of the color change of the reagent in a reagent and LOT/LOT strips 126 and 128 respectively of FIGS. 3 and 6.

Switch 112 is actuated by switch actuator member 114 where the member 114 is positioned above the front housing bottom 116 and behind the front casing 14 as also illustrated in FIG. 4 and as later described in detail.

Also illustrated in FIG. 4 is a friction catch 118 mounted above the back housing bottom 117, and within the back case 16 for receiving and holding in place the switch actuator nodule 120 on the end portion of the disposable diagnostic lancet package 12. An electronics circuit board 54 positions within the medical system 10 along with a piezo electric beeper 122 as illustrated, and is later described in detail in FIG. 8A and 8B.

Figure 5:
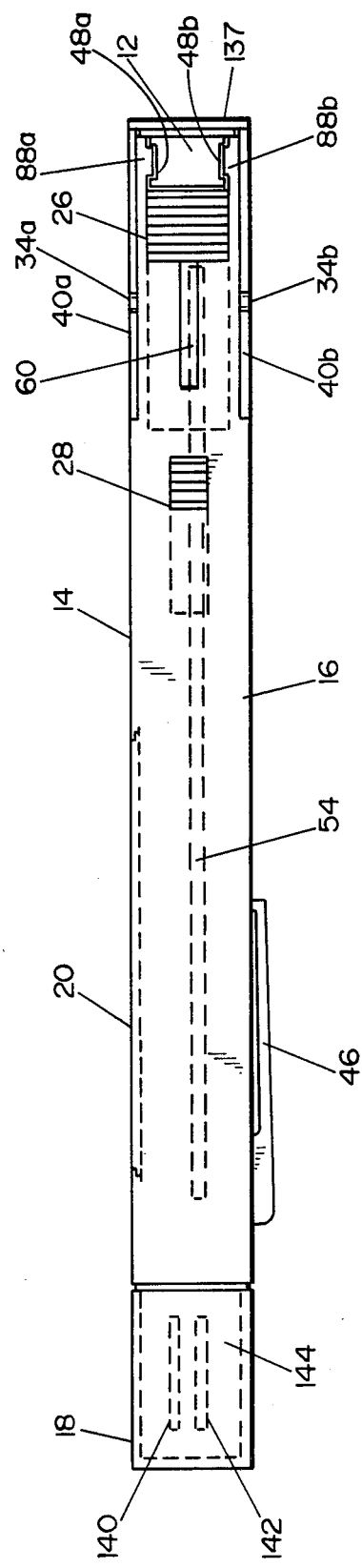
FIG. 5 illustrates a top view of the glucose medical monitoring system.

FIG. 3 illustrates a view taken along line 3—3 of FIG. 1 with the hammer 50 cocked and with a disposable diagnostic reagent-lancet unit 12 positioned in the medical system 10. As previously described, the engagement members 88a and 88b slidably engage within engagement slots 48a-48b of the disposable diagnostic reagent lancet unit 12 respectively, and as also illustrated in FIG. 5. The lancet package 12 positions and engages into a functionally "locked in" position as the bottom plate 124 fits within recesses 40a and 40b. At the same time, the switch actuator nodule 120 pushes the switch actuating member 114 against the actuating arm of the lancet diagnostic unit switch 112 for electromechanically indicating to the electrical circuitry that a reagent lancet diagnostic unit 12 is positioned properly withinthe diagnostic medical system engagement area 56, and that the reagent pad 126 and the LOT/LOT pad 128 are positioned adjacent to the lens 96 for photometer reading. The reagent pad 126 is read through the reagent aperture 130 by the about 5 degrees inwardly canted reagent LED 98 and by the about 30 degrees inwardly canted photo diode 110 sequentially after the LOT/LOT pad 128 is read through LOT/LOT aperture 132 by the about 5 degrees inwardly canted LOT/-LOT 100 and by the about 30 degrees inwardly canted photo diode 110. The hammer 50 and the hammer casing 58 are illustrated in this figure immediately poised to strike the sterile lancet 134 in the disposable diagnostic reagent lancet unit 12. The spring 74 is compressed to power the hammer 50 in the housing 58 to forcefully strike the lancet 134 so that the lancet 134 travels with sufficient force to traverse through the locator hole 136 for puncturing the bottom plate sterility barrier 138 and subsequentially a users skin for drawing of blood. In activating the hammer 50, the hammer release button 28 is depressed dislodging the catch 80 from the catch 78 thereby allowing the spring 74 to propel the hammer 50 within the hammer casing 58 into the lancet 134. The lancet 134 travels on the living spring 158c straight downwardly into the finger in the example. After the users finger is punctured for sampling the blood, the spring 66 about the hammer 50 provides that the hammer 50 is fully retracted back into the hammer casing 58 to a neutral position. The hammer casing 58 is then returned and properly positioned with respect to the predetermined state.

FIG. 4 illustrates an end view of the medical system 10 in partial cross section taken along lines 4—4 of FIG. 1. Particularly illustrated is the floating optics head 52 in tracks 92a-92d, and the positioning of LEDS 98 and 100 which are canted about 5 degrees towards the center. Photo diode 110 in turn is canted about 30 degrees towards the center and towards LED'S 98 and 100 for most effective reading of LOT/LOT strip 128 and reagent strip 126. Also illustrated is the hammer casing 58 within geometrically configured casing tracks 62a and 62b. End views of switch actuator 114 and the switch actuator catch 118 are likewise illustrated in the figure.

FIG. 5 illustrates a top view of the medical system 10 including the electronic circuit board 54 placement longitudinally along the housing axis of the medical system 10. Engagement members 88a and 88b of the diagnostic medical system 10 are illustrated engaging engagement slots 48a-b of the disposable diagnostic reagent lancet unit 12. Batteries 140 and 142 are retained in the battery compartment 144 by a snap on battery retainer cap 18. A pocket clip 146 is mounted on the back housing for securing of the diagnostic medical system 10 in a users pocket. Dust cover 30 has been removed for sake of brevity of the illustration.

Figure 6A:
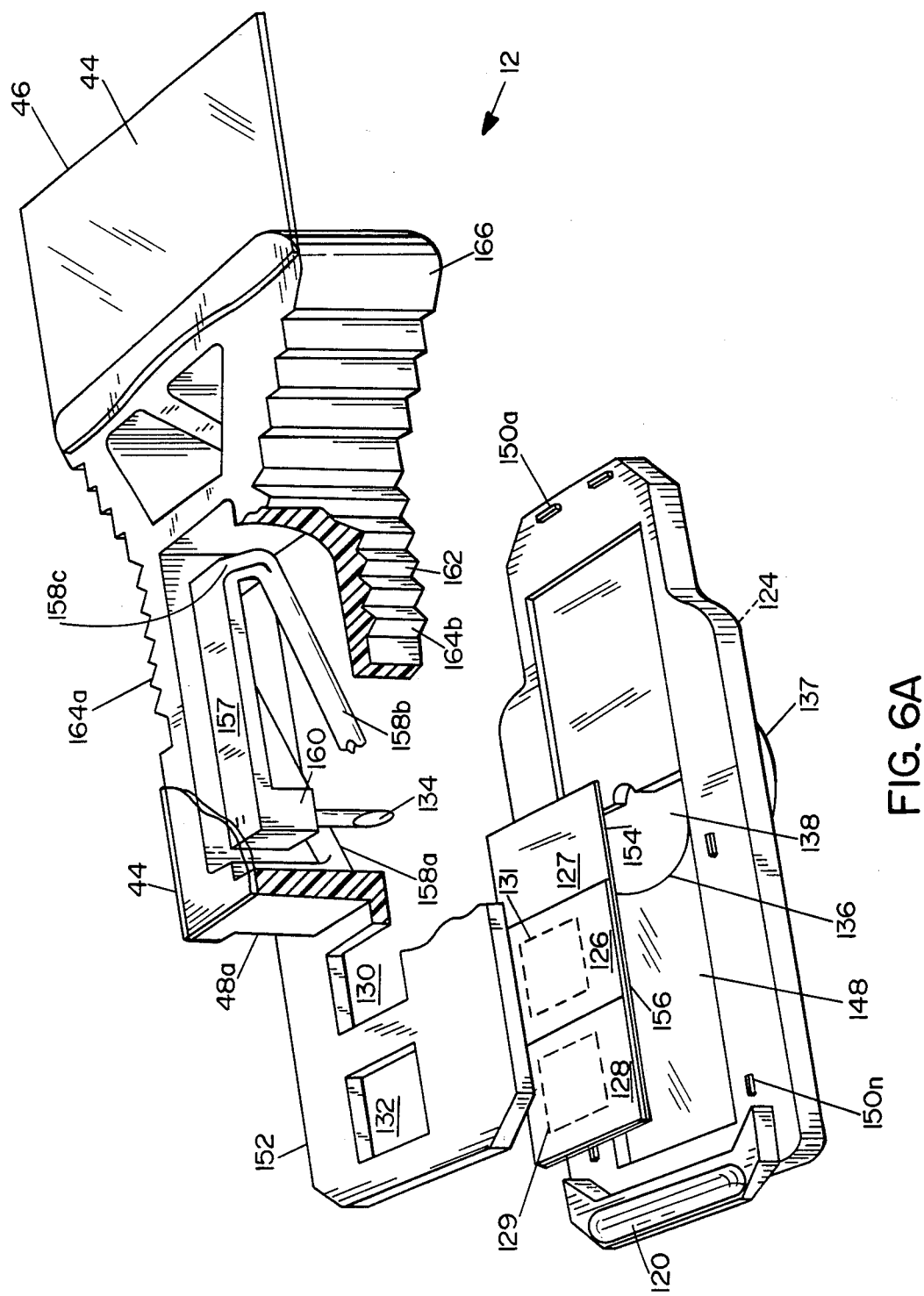
FIG. 6A illustrates a partial cutaway view in perspective of the disposable diagnostic reagent-lancet unit.

FIG. 6A illustrates a partial cutaway view, in perspective, of the disposable diagnostic reagent lancet unit 12. A geometrically configured bottom base plate 124 includes a centrally positioned locator hole 136, a substantially rectangular multi layer cavity 148, a puncturable sterility barrier 138 affixed within cavity 148, a switch actuator nodule 120 for subsequent actuation of switch 112, and a plurality of energy directors 150a-150n for ultrasonically bonding the bottom plate 124 to the main body member 152 of the unit 12. Wicking material 154, erythrocyte barrier 156, reagent pad 126, lot/lot pad 128, and double sided tape 127 including cutouts operations 129 and 131 are illustrated as fitting into the lower portion of cavity 148. The main molded body member 152 includes lot/lot aperture 132 and reagent aperture 130, lancet torsion bar 157, lancet springs 158a and 158b with a modulus of elasticity, a living hinge 158c, a lancet mount 160, a lance 134, a rectangularly grooved shaped lancet housing 162 and positioning handle 166. The member 152 is ultrasonically bonded or otherwise secured over the reagent pad 126, lot/lot pad 128, erythrocyte barrier 156, wicking 154, double sided tape 127 and the sterility barrier 138 to the bottom plate 124 as illustrated. A donut shaped fluid channeling member 137 positions on the lower surface of bottom plate 124 surrounding locator hole 136 for insuring isolation of the blood sample and for capturing the blood within the confines of the channeling member 137 including locator hole 136 so that as much blood as possible is retained in the locator hole area. This proper blood sample is transported by wick assembly 154 to reagent pad 126 and LOT/LOT pad 128. Engagement slots 48a and 48b position longitudinally along the sides of the lancet spring housing as well as the multiple grooved finger grasping surfaces 164a-164b extending along a geometrically configured positioning handle 166. A pull off removable polyester sterility barrier 44 including pull tab 46 positions as illustrated on the lancet spring housing 162 for insuring and maintaining sterility of the disposable diagnostic reagent lancet unit 12 prior to use and engagement within the medical system 10.

The color development in the reagent pad is monitored electrically from the side of the pad opposite to that which is in contact with the wicking material by way of example and for purposes of illustration only. To eliminate color interference potentially caused by red blood cells, reflective pigment particles are incorporated into the separation membrane to mask and filter any red cells effects from the light reflected to the electronic sensing circuitry.

Chemical composition of each reagent pad, by way of example and for purposes of illustration and not to be construed as limiting of the present invention, is as follows:

| | |
|---|---|
| O-tolidine | 37.5 micrograms |
| Glucose oxidase | 0.20 u |
| Peroxidade | 1.40 u |
| Buffer such as citrate | 240 micrograms |
| Non-Reactive Ingredients | 96 w/v % |

One principle of operation for the reagent lancet 12 is as follows:

A. The hammer-spring is cocked by movement of the sliding door into the locked open position.

B. The Glucose Medical Monitoring System 10 and Disposable Diagnostic Reagent-Lance Unit 12 are engaged for properly aligning the apertures.

C. A deliberate, manual activation of the lancet release button actuates the hammer-spring.

D. The hammer-spring travels forcefully and strikes the lancet with enough force to drive the lancet through the locator hole and into the user's skin.

E. Properties of the plastic "spring board" to which the lancet is attached allow through the swift retraction of the lancet from the user's skin to the lancet's original position.

For user safety, the finger-puncture device is designed such that:

1. Lancet actuation is permitted only by deliberate manual activation of the lancet release button.
2. Alignment of aperture is insured by mechanical stops and detents.
3. Depth of lancet penetration is limited to about 2.2 mm by mechanical stops.
4. The lancet is kept sterile by individual packaging of each disposable diagnostic medical system in foil.

Each diagnostic unit 12 contains a chemistry/wick component designed to absorb a drop of whole blood, and transport the blood to a dry chemistry reagent pad. The reagent pad filters red blood cells and reacts colorimetrically with blood glucose in a manner like dry glucose sensing chemistry from Ames (Dextroxtix), BioDynamics (Chemstrip) and Kodak (Ektachem 400 Clinical Chemistry Slide for Glucose).

One principle of operation of the glucose sensing chemistry is as follows:

A. A sample of whole blood is touched to absorbent wicking material (or like textile) which applies the blood to a wick/reagent pad interface.

B. At the interface the sample permeates the first layer of the reagent pad, which effectively filters interfering red blood cells.

C. Plasma from the sample is allowed to penetrate to a second reagent pad layer which contains reagents specific for a glucose detection reaction.

D. Glucose in the sample is oxidized by atmospheric oxygen with the aid of glucose oxidase, and enzyme specific for glucose (the end products of this reaction are gluconic acid and hydrogen peroxide).

E. In the presence of the enzyme peroxidase, hydrogen peroxide produced in step D oxidizes o-tolidine (an indicator normally present in reduced form).

F. The amount of color formed in step E is proportional to the amount of glucose present in the sample.

G. The electro-optical system detects the color formed in the above reaction and converts a reading to a glucose concentration signal.

The above steps D-F are summarized by the chemical notation:

Glucose Oxidase

Glucose+$O_2$ ... Gluconic Acid+$H_2O_2$

Peroxidase

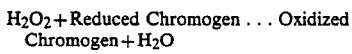

$H_2O_2$+Reduced Chromogen ... Oxidized Chromogen+$H_2O$

REAGENT COMPONENT TABLE

1. Textile (wick)—Woven linen or non-woven polyester/wood pulp blend. Cotton can also be used.
2. Adhesive—Double-sided transfer tape or coated plastic, such as Mylar. Pressure sensitive.
3. Cellulose Acetate (Reagent Pad)-Ultrafiltration membrane with uniform pore size. The pores can be about 0.45 microns.
4. Paper with dye coloring (Lot to Lot code pad).
5. Erythrocyte Barrier—Upper surface portion of cellulose acetate.
6. Active Reagents:

| | |
|---|---|
| a. Glucose oxidase | 0.20 units |
| b. Horseradish peroxidase | 1.40 units |
| c. Ortho-tolidine | 37.5 micrograms |
| d. Sodium citrate buffer | 240 micrograms |

7. Non-reactive ingredients—96 w/v % (preservatives, bacteriostat, etc.)

REAGENT SYSTEM-REAGENT PAD

A. Plasma from blood sample enters reagent pad;
B. Glucose enters reagent pad with plasma; and,
C. Glucose plus active ingredients product oxidized ortho-tolidine/blue color.

FIG. 6B illustrates an exploded view including bottom wicking 154, double sided adhesive tape 127, cutouts 129 and 131 in the double sides adhesive tape 127, and reagent and LOT/LOT pads 126 and 128 respectively including erythrocyte barrier 156.

Figure 7:
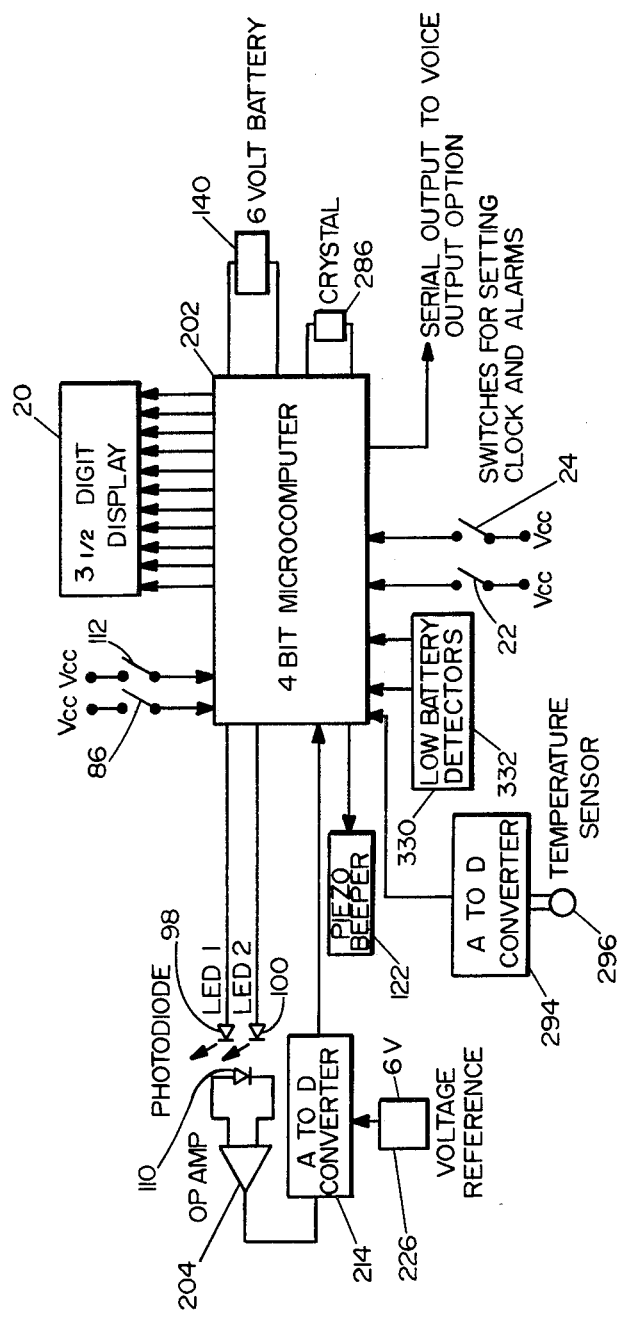
FIG. 7 illustrates an block diagram of the glucose medical monitoring system.

FIG. 7 illustrates a electronical block diagram 200 of the glucose medical monitoring system 10. All numerals correspond to those elements previously described and as now described in FIG. 8.

Figure 8B:
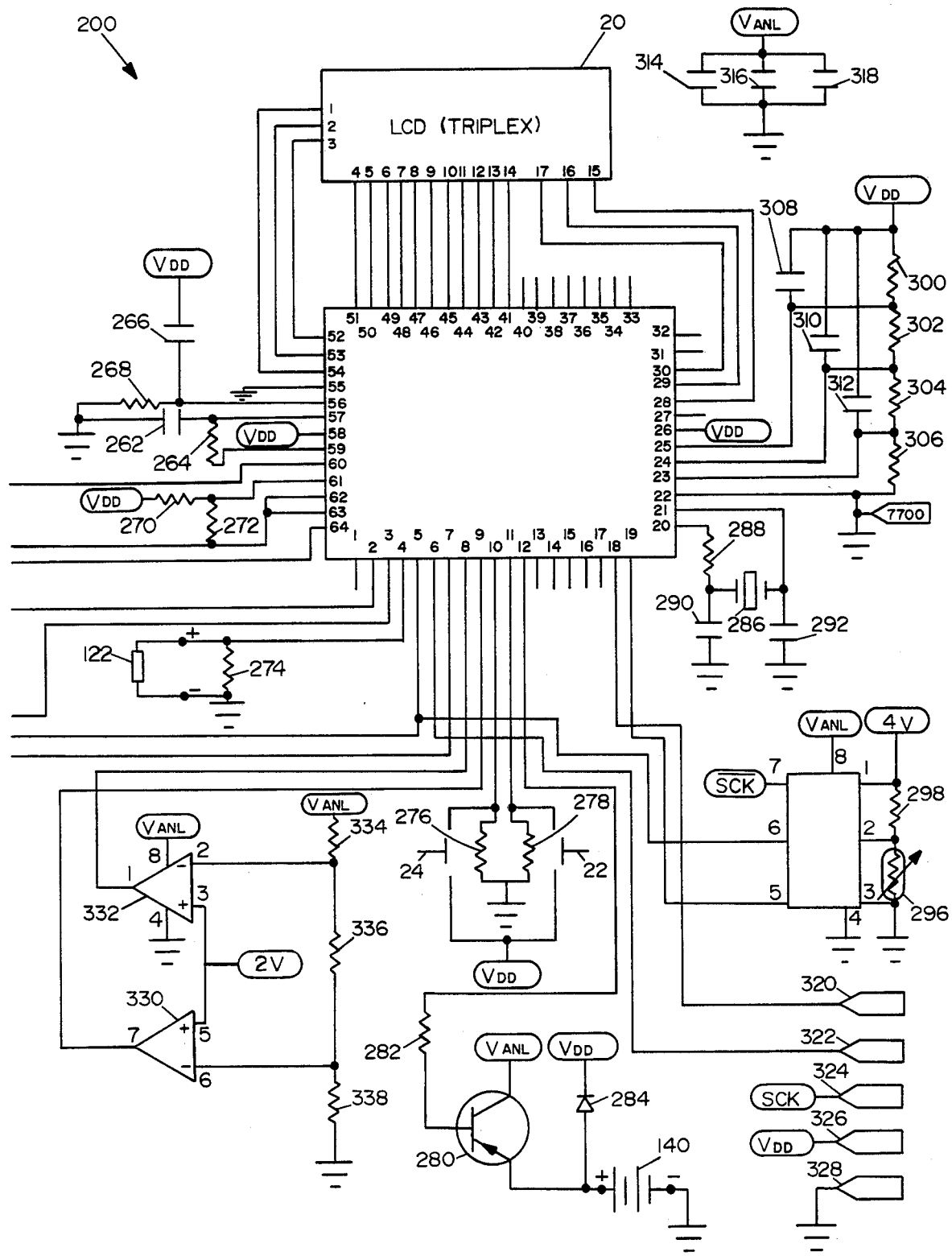

FIGS. 8A AND 8B illustrate the electrical circuit schematic package diagram 200 including the digital display 20, clock and alarm switches 22 and 24, light emitting diodes 98 and 100, photo transistor 110, switch 86, lance switch 112, piezo electric beeper 122, and batteries 140 and 142. A high gain op-amplifier 204 including, op-amp feedback capacitor 210, and op-amp pullup resistor 212 are for the amplifier circuit. A to D converter 214, lower voltage reference voltage divider resistor 216, lower voltage reference voltage divider potentiometer 218, inverter transistor 220 for clock for A to D converter 214, pullup resistor 222 for inverter 220, inverter transistor base drive resistor 224, voltage reference regulator integrated circuit 226, voltage reference regulator input bypass capacitor 228, output adjustment resistor 230, output adjustment resistor 232, output adjustment potentiometer 234, output filter capacitor 236, voltage divider resistor 238, and voltage divider resistor 240 are for the A to D conversion of the several colorimetric change of the reagent and the voltage reference regulator. Switching transistor 242 for LED 100, switching transistor 244 for LED 98, switching transistor base drive resistor 246, and switching transistor base drive resistor 248 are for switching the LED's. LED 98 brightness adjustment resistor 250, LED 98 brightness limiter resistor 252, LED 100 brightness adjustment resistor 254, and LED 100 brightness limiter resistor 256 are for compensating the LED's. RC oscillator circuit capacitor for microprocessor clock 262, RC oscillator circuit resistor for microprocessor clock 264, reset capacitor 266, and reset resistor 268 are for the microprocessor 202. An optional jumper 270 provides for selecting either unit of measure mg/dl (U.S.) or mmol/l (Europe). Pulldown resistor 272, piezo electric beeper impedance load resistor 274, microprocessor pulldown resistor 258, microprocessor pulldown resistor 260, microprocessor pulldown resistor 276, microprocessor pulldown resistor 278, analog power switching transistor 280, switching transistor base drive resistor 282, reverse voltage protector diode 284, 32.768 KHZ crystal for timer 286, timer current limiter resistor 288, crystal oscillator capacitor 290, and crystal oscillator capacitor 292 are for the microprocessor 202. A to D converter 294 for temperature variations, thermistor 296, and voltage divider resistor 298 are for the temperature sensing circuit. LCD bias resistors 300-306, and LCD bypass capacitors 308-312 are for the LCD display 20. Serial data output enable jack 320, serial data output jack 322, and serial data clock jack 324 are for external connections such as to a personal computer. Power jack 326, ground 328, bypass capacitors 314-318, low battery comparator 330, very low battery comparator 332, and comparator voltage dividers 332-338 are for power supply circuitry.

The operation of the electrical circuitry of FIGS. 8A and 8B is now described.

LED 98 is the light source that illuminates the reagent chemistry area. The reagent chemistry changes color in proportion to the amount of glucose in the blood. The light from LED 98 reflects off the chemistry and is sensed by photodiode 110. This signal is amplified by a high gain op-amp 204 U3, and then sent to the input of the analog to digital converter 214. The analog signal is converted to a digital signal for use by microprocessor 202. The software algorithm in microprocessor 202 processes this information, and then outputs a blood glucose measurement to the liquid crystal display 20.

LED 100 is the light source that illuminates the lot to lot indicator on the medical monitoring system 10. This provides information to the microprocessor 202 to correct for variations in different lots of chemistry. The lot to lot indicator also is used to determine if blood has completely covered the reagent chemistry. The reflected light from LED 100 is sensed by photodiode 110, and the signal is sent to the microprocessor 202 in the same way as light reflected from LED 908.

Voltage reference regulator 226 provides a reference voltage for the medical monitoring system circuitry. The reference voltage is used by the analog to digital converter 214, the low battery detection comparators 330 and 332 circuitry, temperature A to D converter 294 and also to keep the LED outputs constant.

Comparators 330 and 332 are used to provide a low battery and very low battery signal to the microprocessor 202. Switching transistor 201 is used to control the power to the analog circuitry which is turned on only when the photodiode 110 sensing circuits are active. A crystal 286 provides a precision clock to the microprocessor 202 for the various timing functions. Switch 112 is used to initiate a blood glucose measurement sequence by the medical monitoring system 10. Switch 86 provides the microprocessor 202 with a signal to tell when a diagnostic lancet unit 12 is inserted. Switches 276 and 278 are used to set the clock and four alarms on the medical monitoring system 10. The piezo electric beeper 122 provides an audible beep to indicate test progress or error conditions. Thermistor 296 with A to D converter 294 provide temperature correction input data to microprocessor 202 to correct for ambient temperature variations which may occur in the user's environment.

Figure 9:
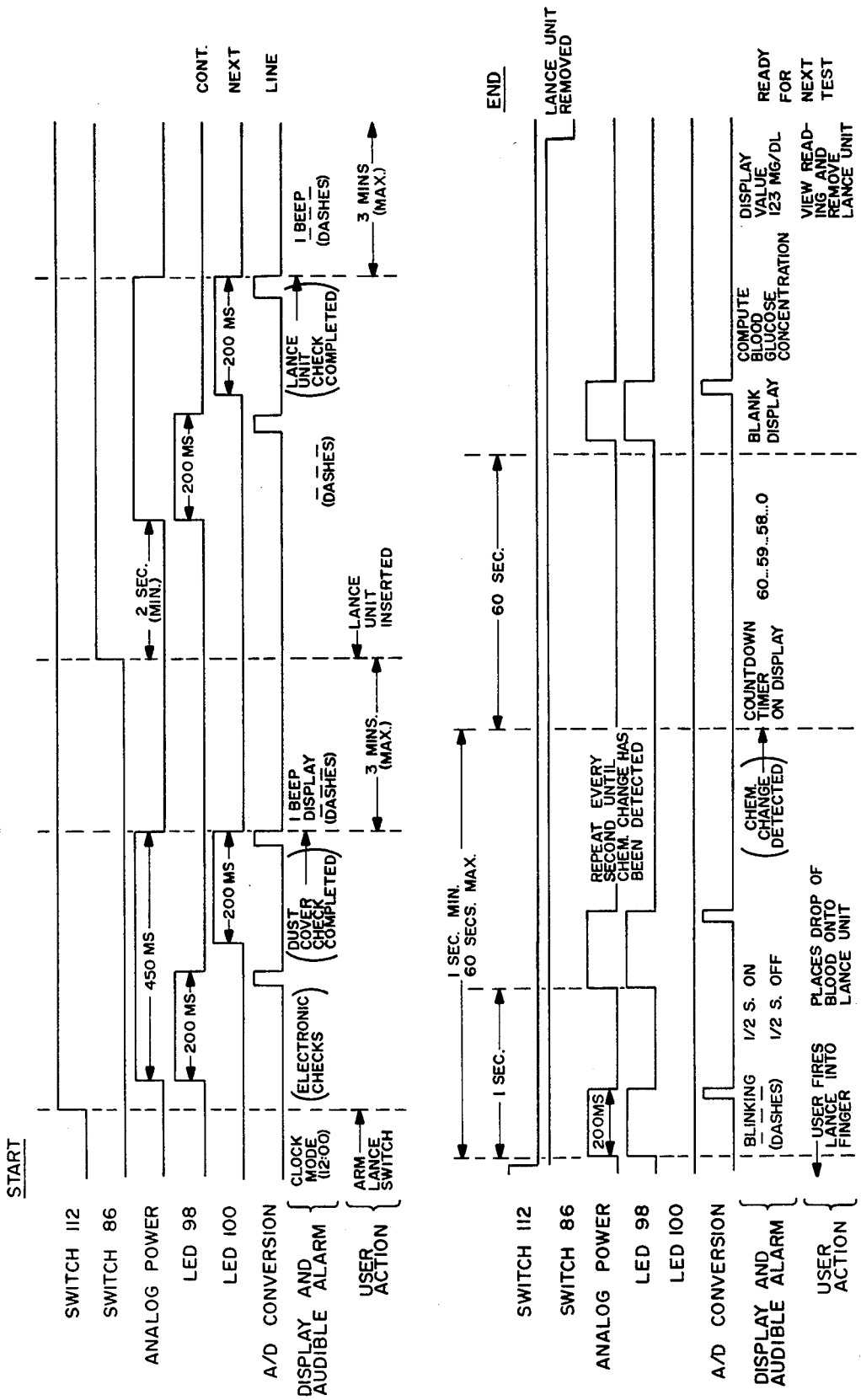
FIG. 9 illustrates a timing chart for the circuitry of the glucose medical monitoring system.
Figure 10A:
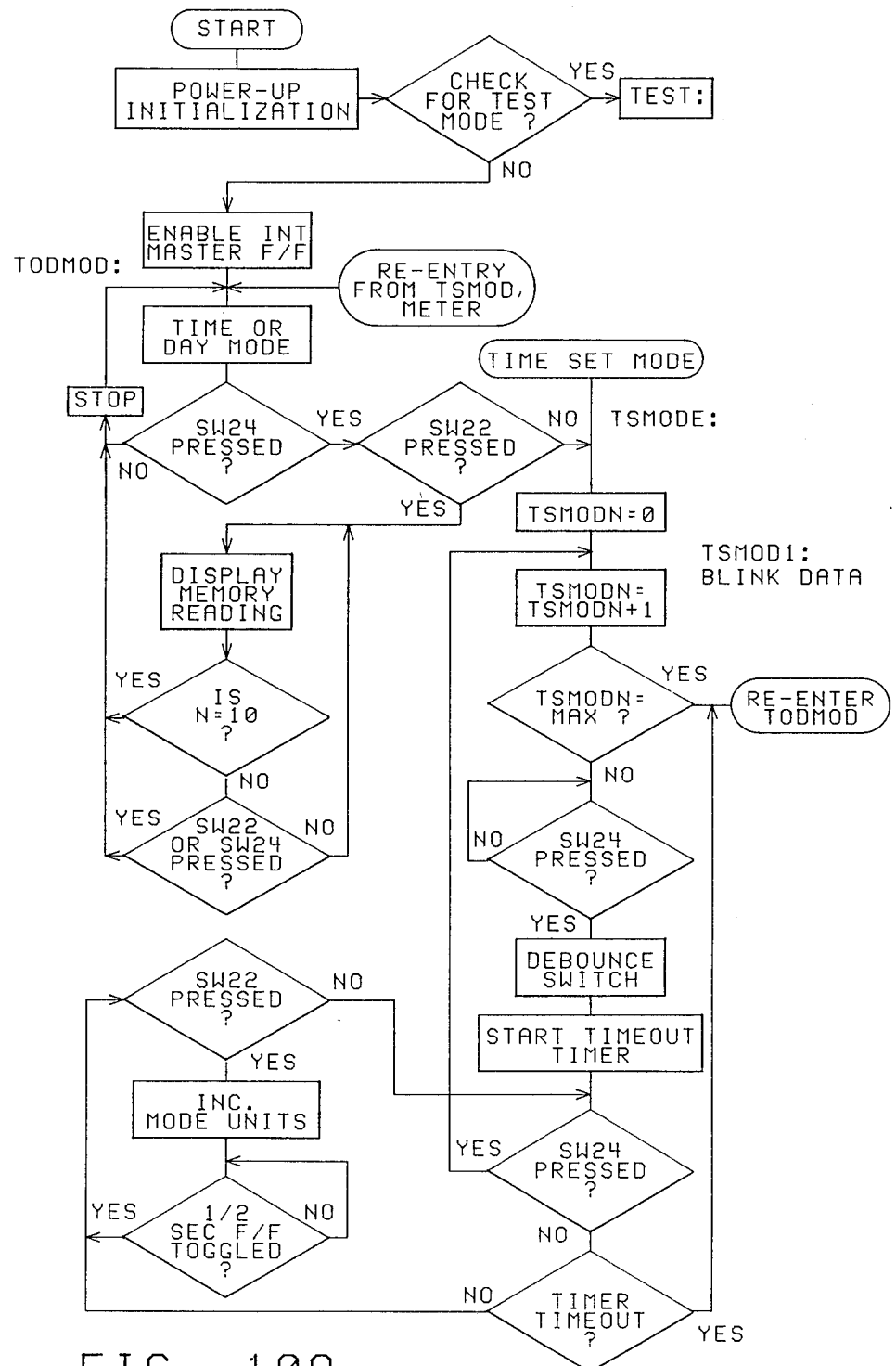
FIGS. 10A, 10B, 10C, 10D and 10E illustrate the flow chart for the glucose medical monitoring system.
Figure 10B:
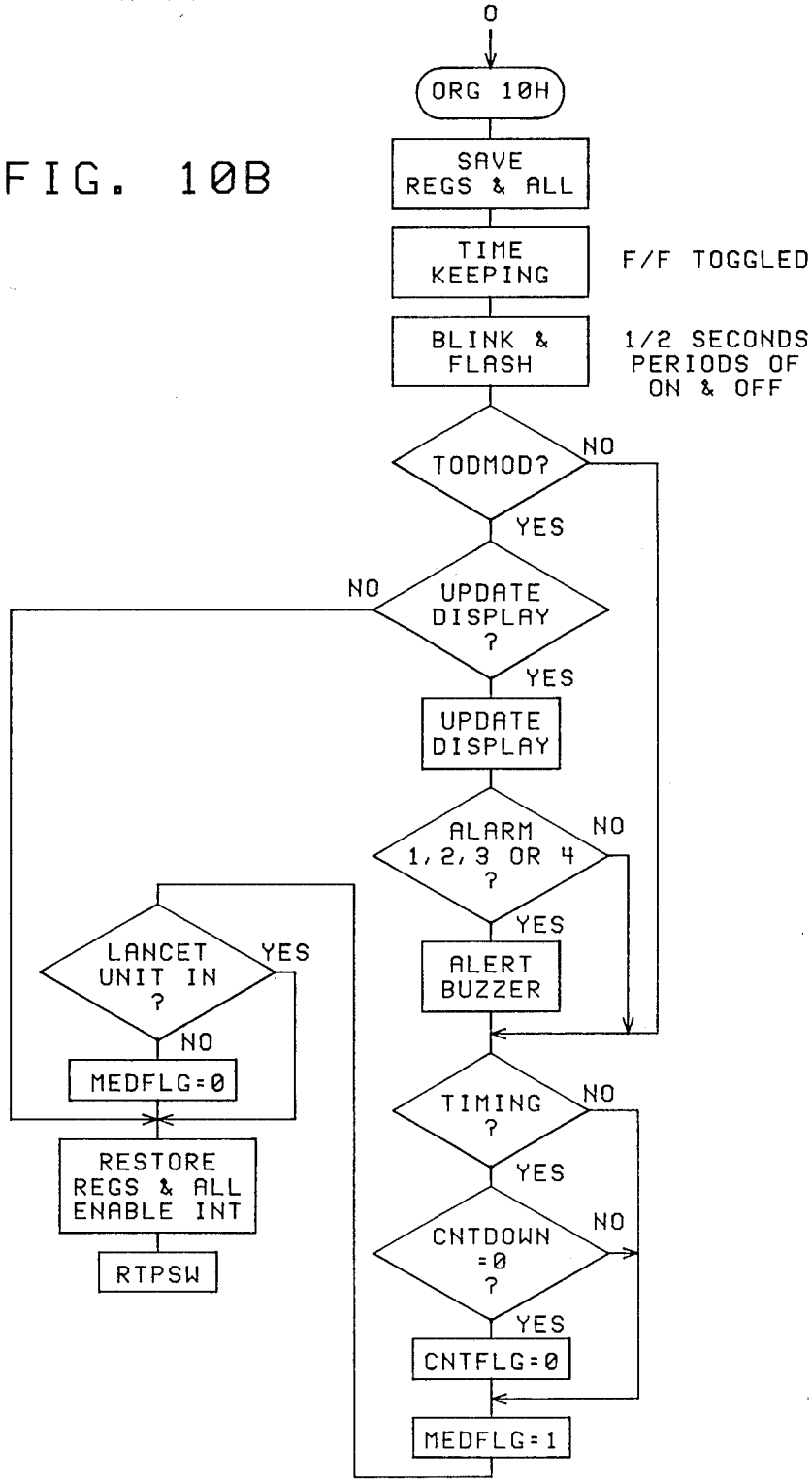
Figure 10C:
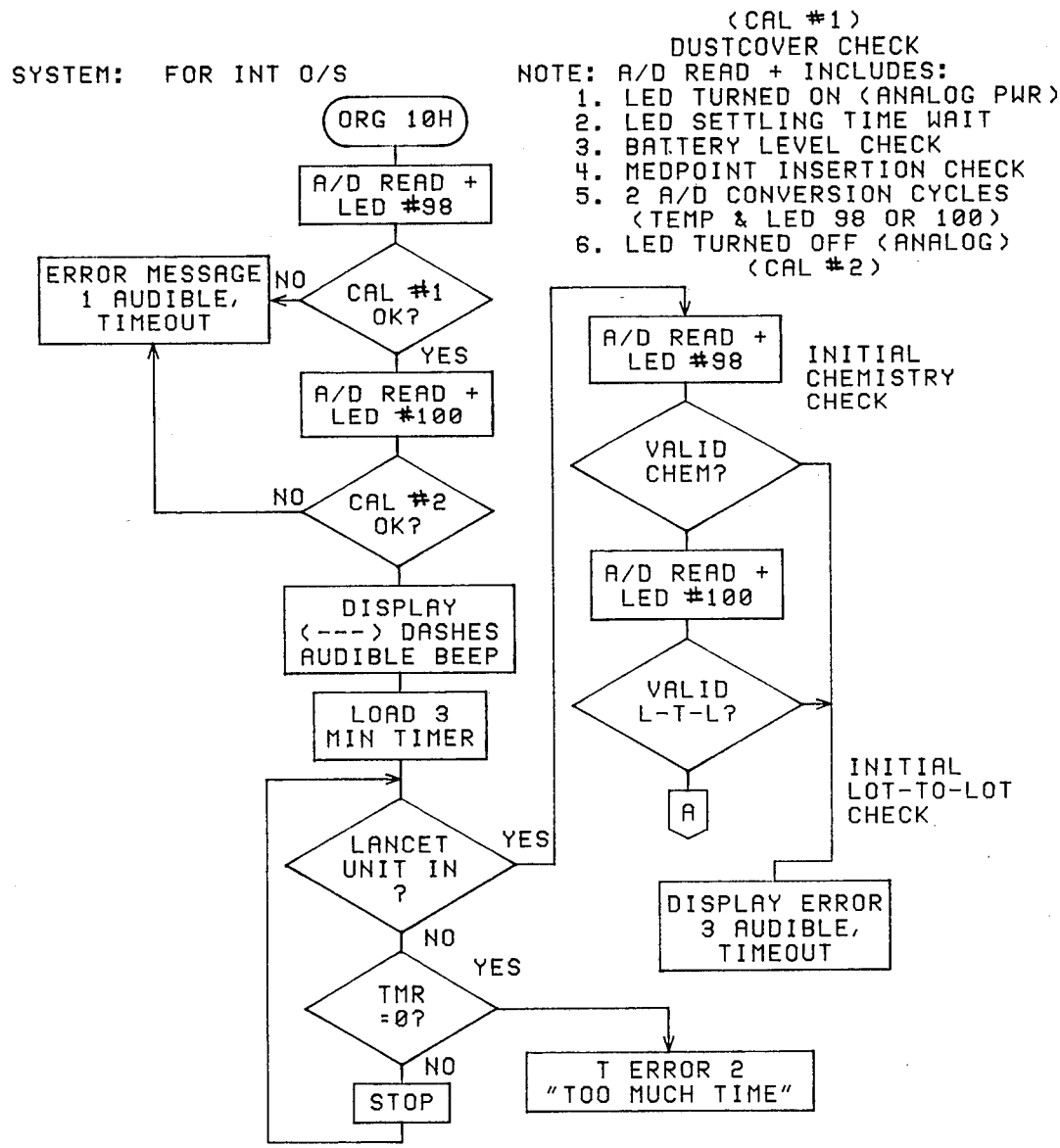
Figure 10D:
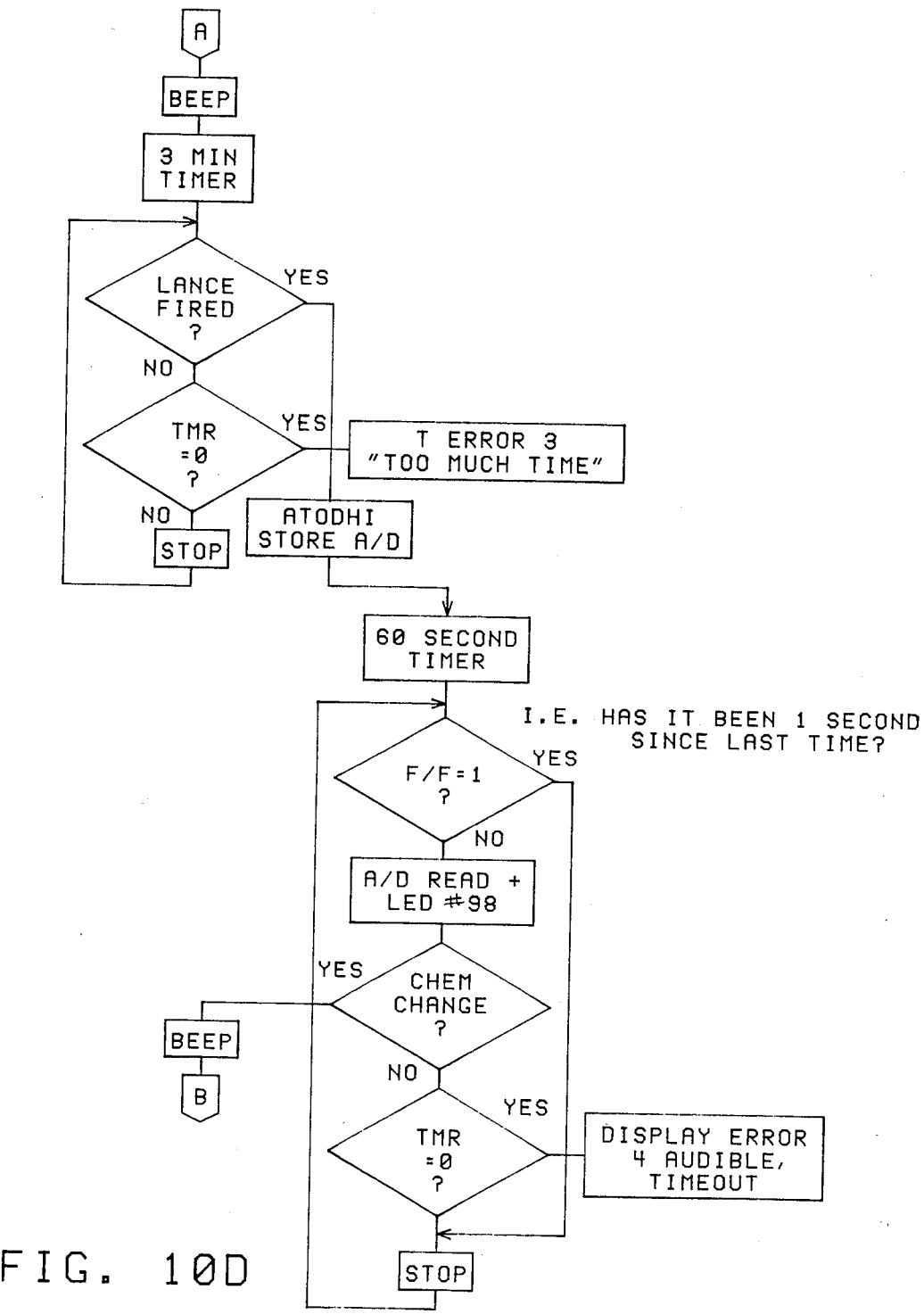
Figure 10E:
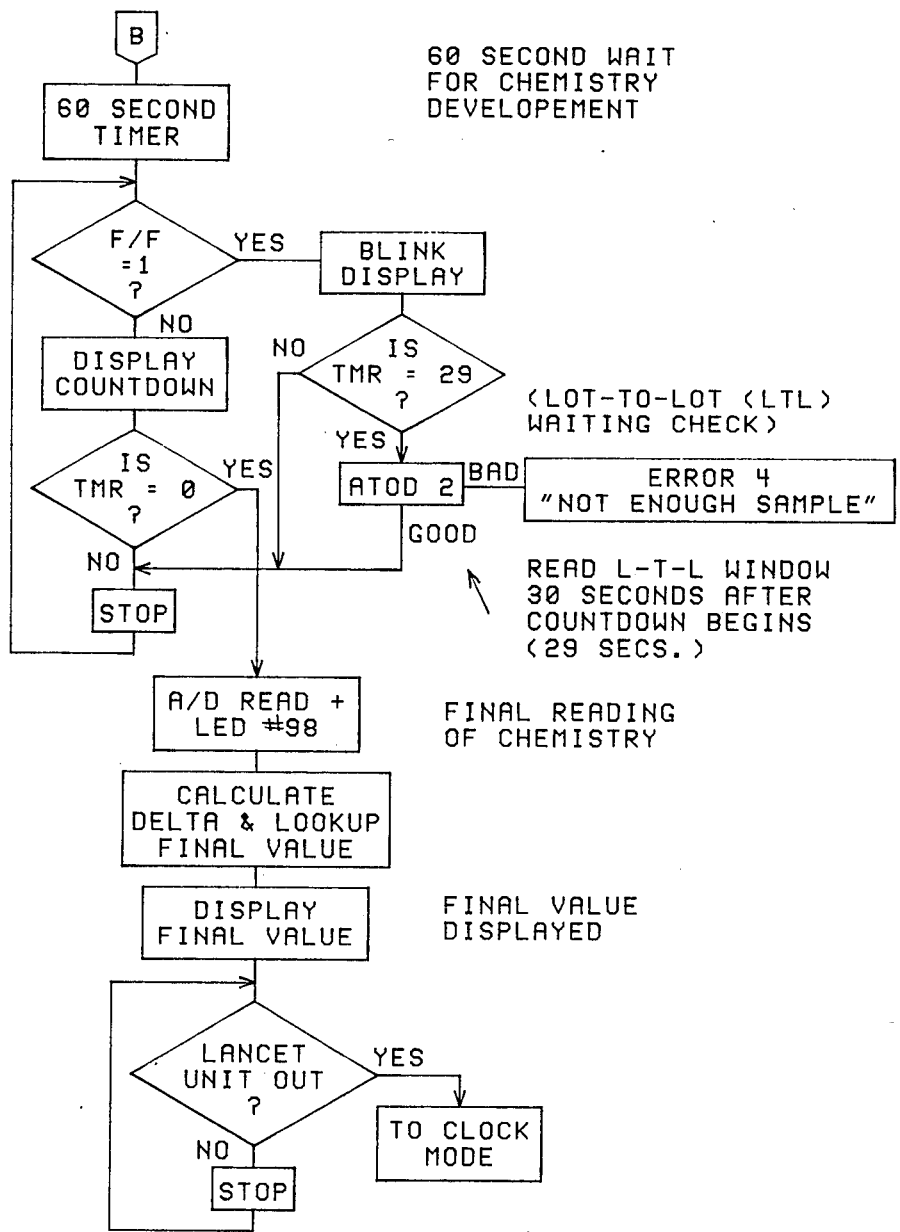

FIG. 9 illustrates the timing diagram for the glucose medical monitoring system of the circuitry of FIG. 8.

FIGS. 10A-10E illustrate flow charts for the glucose medical monitoring system and operation steps corresponding to the flow chart are further described in FIGS. 11A-11D.

FIGS. 11A-11D describe procedural operation and steps including describing in the left hand column what the user does and in the second to the left end column describing electromechanical and electrical operation. The display column represents what the user sees and the audio beep column represents what the user hears. FIG. 11C indicates the error messages which could appear on the display. FIG. 11D illustrates a listing of the notes corresponding to FIGS. 11A and 11B.

MODE OF OPERATION

The operation of the glucose medical monitoring system is as follows:

1. ENSURE THE DUST COVER IS IN PLACE.
   The first step in a glucose medical monitoring system measurement is electronic calibration. This procedure is done automatically by the glucose medical monitoring system; but, to work properly, the dust cover must be in place before the beginning of each measurement. If the dust cover is not in place, i.e. closed, swing it shut until it clicks.
2. OPEN THE SLIDING BUTTON.
   Open the sliding button on the side of the glucose medical monitoring system and lock it into position. " - - - " should appear on the display at this time.
3. OPEN THE DUST COVER.
   Open the dust cover by grasping it, and swing it into the locked position.
4. INSERT A FRESH DISPOSABLE DIAGNOSTIC REAGENT LANCET UNIT INTO THE GLUCOSE MEDICAL MONITORING SYSTEM.
   Insert a fresh disposable diagnostic reagent lancet unit into the glucose medical monitoring system by grasping the tip by its serrated edges, and sliding it into the slot previously occupied by the dust cover. The glucose medical monitoring system will perform a second calibration (chemistry calibration), and one of two things will happen:
   A. The disposable diagnostic medical system will settle into place correctly, and the glucose medical monitoring system will beep once and display " - - - ". In this case proceed with step 5, being careful not to jar the disposable diagnostic medical system from this position as one continues.

B. The glucose medical monitoring system will beep three times and either "EEE" or "EEE" will appear on the display, meaning a problem has occurred in chemistry calibration.

5. HOLD THE GLUCOSE MEDICAL MONITORING SYSTEM IN ONE'S HAND.

Take the glucose medical monitoring system with attached disposable diagnostic unit, and hold it in either hand as one would hold a pen or a pencil with the lancet release button facing up. One has three minutes to accomplish steps 5-7, or else the glucose medical monitoring system will automatically error out.

6. CENTER THE GLUCOSE MEDICAL MONITORING SYSTEM OVER THE PUNCTURE SITE.

Center the glucose medical monitoring system/disposable diagnostic unit combination over the skin area to be punctured, and press the disposable diagnostic medical system locator hole to ones finger with moderate pressure.

7. ACTIVATE THE LANCET.

Activate the lancet by pushing the lancet release button with one's index finger. Once the lancet has been activated, one has 60 seconds to obtain an adequate blood sample. The LCD display will blink " - - - " on and off every second until an adequate blood sample is obtained or the 60 seconds has elapsed.

8. OBTAIN A LARGE DROP OF BLOOD ON YOUR FINGERTIP.

Massage one's finger in a milking fashion to help form a large drop of blood on one's fingertip. A large drop of blood is needed for the disposable diagnostic medical system to properly carry out the glucose chemical reaction.

9. TOUCH THE WICKING MATERIAL TO THE DROP OF BLOOD.

After a drop of blood has formed, touch the special wicking material, found at the edge of the locator hole, to one's fingertip to absorb the blood. Touch the drop of blood to the wicking material as soon as it forms.

10. LISTEN FOR THE GLUCOSE MEDICAL MONITORING SYSTEM TO BEEP.

Continue milking blood onto the wicking material. When one hears a single beep and observes the glucose medical monitoring system display change from the blinking three dashes " - - - " to a 60 second countdown sequence, one has successfully obtained a blood sample and may go onto the next step. If one is unable to get enough blood onto the wicking material in the 60 seconds allotted, the glucose medical monitoring system will beep three times and "EEE" will appear on the display.

11. REMOVE THE GLUCOSE MEDICAL MONITORING SYSTEM FROM ONE'S FINGER.

Once the glucose medical monitoring system has beeped and shown the countdown sequence to indicate a sucessful sample, one is free to remove it from the skin or fingertip. Do not remove the disposable diagnostic unit at this time as it is being used by the glucose medical monitoring system to perform the rest of the analysis.

12. RECORD YOUR BLOOD GLUCOSE LEVEL.

After 60 seconds, the glucose medical monitoring system will beep once more, and display the glucose concentration of your blood in units of mg/dl. Promptly record the displayed value in the logbook. The glucose level will remain on the glucose medical monitoring system display for 60 seconds or until the disposable diagnostic reagent-lancet unit is removed.

13. REMOVE THE DISPOSABLE DIAGNOSTIC MEDICAL SYSTEM.

Once you have recorded your blood glucose level, remove the disposable diagnostic unit by grasping it by its serrated edges and pulling. Dispose of the used disposable diagnostic unit in an appropriate manner.

14. TO OBSERVE PREVIOUS MEASUREMENTS.

Hold both clock buttons down for several seconds to begin showing results from measurements stored in its memory. The first memory result shown will be from the measurement just taken. It will remain on the display for a total of five seconds and be accompanied by an M (for Memory) and a 1 (for most recent result), i.e. "$^M100^1$". After five seconds, the value of the second-most recent memory measurement will appear accompanied by an M and a 2 "$^M123^2$". This process will continue until a total of 10 memory results have been displayed.

15. REPLACE THE DUST COVER.

Snap the dust cover back into place to keep the glucose medical monitoring system clean while not in use.

Hygiene:

A. Infection barrier.

The only part touching the patient is the wick of the disposable diagnostic unit and the bottom plate.

Actuator:

There is a mechanical detent at the "destination/cocked" end of the travel of the actuator. Once the actuator is moved to either end position, it will remain in that position until triggered by some other action. The actuator is mechanically linked to the hammer spring. The actuator will automatically return to the "original/uncocked" position if the operator lets go of it before reaching the mechanical detent at the other end of travel.

Actuator Must be Fully Open:

In order for the user to "operate" the lance release push button; i.e., the push button is mechanically locked to the actuator so that the button cannot be "operated" if the actuator is not in the fully open position if the operator lets go of it before reaching the mechanical detent at the other end of travel.

Once the Hammer Spring is Cocked:

A. The lancet release push button can be depressed/operated; with or without a disposable diagnostic unit engaged.

B. The only way to close the actuator is to depress/operate the lancet release push button with or without a disposable diagnostic unit engaged.

C. The actuator will automatically return to its original position, when the lancet release button is depressed/operated.

When a Disposable Diagnostic Unit is Fully Engaged

A. It is retained in that position by mechanical detent to minimize (not prevent) inadvertent movement by the operator once a measurement sequence is in progress.

B. If sufficient force is applied, accidental or deliberate, the disposable diagnostic unit can be moved and in fact removed from the glucose medical monitoring system at any time. If this happens, the switch contacts will open resulting in an error condition, whether or not the sensing circuits are active at that same time.

The Hammer can be Fired:
A. With or without a disposable diagnostic unit inserted.
B. With or without the dust cover in place.

The Dust Cover can be Field Replaceable by the End User.

Self Calibration:
A. Predefined color standard in dust cap to validate disposable diagnostic unit performance.
B. Production lot variations.
C. Unreacted reagent strip.

Interrupt, User Controlled:
The user shall be able to perform an "interrupt" (exit from an error condition without awaiting automatic power down) by either (A) or (B):
A. Opening switch 1 contacts (if they are not already open) and then closing them again . . . AND
Removing the disposable diagnostic unit if it is engaged (so that dust cover can be rotated back to its original closed position) . . . AND Rotating the dust cover back to its original closed position so that the first step of electronic calibration can be performed.

DISPOSABLE DIAGNOSTIC REAGENT LANCET UNIT

Disposable diagnostic reagent lancet unit chemistry units are designed for use with the glucose medical monitoring system in the determination of glucose concentration in whole blood. Built into each disposable diagnostic medical system tip is the following:

(1) A locator hole to use when centering the disposable diagnostic medical system on your fingertip or skin.
(2) A sterile lancet for finger puncture.
(3) A chemistry reagent pad, site of a glucose chemical reaction.
(4) Highly absorbent wicking material to collect a blood sample and apply it to the reagent pad.

Chemical Composition:

| O-tolidine | 37.5 micrograms |
|---|---|
| Glucose oxidase | 0.20 u |
| Peroxidase | 1.40 u |
| Buffer | 240 micrograms |
| Non-reactive ingredients | 96 w/v % |

Chemistry Test Principle

The reagent and wick component of the disposable diagnostic unit is designed to absorb a drop of whole blood, and apply it to a dry chemistry reagent pad where a colorimetric chemical reaction occurs between the chemicals in the pad and glucose in the user's blood. The chemical reaction is then analyzed by the glucose medical monitoring system and displayed in units of mg/dl on the glucose medical monitoring system display.

The chemical reaction is based on the glucose oxidase method of determining blood glucose levels. Glucose oxidase catalyzes the oxidation of glucose in a blood sample, producing gluconic acid and hydrogen peroxide. In the presence of the enzyme peroxidase, the hydrogen peroxide oxidizes an indicator reagent (normally present in the reduced form) producing a blue color in the reagent pad. The amount of blue color produced by the reaction is proportional to the amount of glucose present in the blood sample and is measured photometrically by the glucose medical monitoring system.

FIG. 12A illustrates a disposable diagnostic reagent lancet unit 500 including a molded plastic bottom plate 502, and an aperture 504. An aperature 506 is provided for application of a blood sample and disposed thereover is a wick 508, and a reagent system 510 including a filter impregnated with the glucose enzyme. The wick 508 also serves as a light block to prevent light from impacting the optics. The separate apertures provide for lancet punctuation as well as application of the blood sample. The wick can be included in the system for transporting the blood sample to the reagent system. The actual transporting of blood is done manually by milking the finger, and then disposing the aperture 506 over the blood which has been milked from the finger or any other skin location.

FIG. 12B illustrates a disposable diagnostic reagent lancet unit 520 including a molded plastic bottom plate 522, and an aperture 524 of just enough internal diameter for the lancet to pass through. An aperture 526 is provided for application of a blood sample to a reagent system 528, including a filter impregnated with an enzyme. There is no wick included in this particular embodiment. The blood sample is applied directly from the finger to the reagent system through aperture 526.

FIG. 13A illustrates a sectional view of another alternative embodiment of a disposable diagnostic reagent lancet unit 602 for the glucose medical monitoring system. The unit 602 includes a housing 630, an opaque top cover 632, and an opaque bottom cover 634. A hammer aperture hole 636 is disposed opposite of wick aperture hole 638. A lance 640 with a point 642 and including a spring member 644 secures at one end to the housing 646. Wick and filter member 648, as later described in detail, mounts between members 632 and 634 and within housing members 630a and 630b. The wick 648 transports by wicking action blood or liquid from the lancet 640 to a reagent strip 650 protected by a transparent plastic cover 652 where LED 612 and photodiode 614 measure color reference readings to be processed be the microprocessor. Optional covers 654 and 656 with peel off adhesive can be applied to the top and/or bottom covers 632 and 634 providing sterility for the lancet 640. Also, the wicking material member 648 can provide sterility protection to the lancet in not having an aperture hole in the material where the material would be a solid piece or material. The wick aperture 638, which is optional, and cover aperture 657 position over the finger in this example for taking a blood sample for determining glucose levels as illustrated in the figure.

FIG. 13B illustrates an end view in partial cross section of the diagnostic point unit 602 where all numerals correspond to those elements previously described. The opposing channel members 658a and 658b provide for insertion into the channels.

Various modifications can be made to the present invention without departing from the apparent scope thereof. Memory values could be displayed by a user on demand and any numbers of memory values could be stored based on the programming. The averaging of memory values could be deleted based on programming. The hammer and hammer actuator can be two separate parts. Any switchable microprocessor can be utilized.

We claim:

1. A disposable diagnostic lancet reagent unit for operative engagement with a glucose medical monitoring diagnostic system, said system including a hammer means, said disposable unit comprising:
   a. a housing;
   b. means for operatively connecting said unit to said system;
   c. puncturing means supported within said housing and aligned to be actuated by the hammer means and driven from within said housing through a first opening therethrough to puncture a surface adjacent said housing and cause a flow of liquid from said punctured surface;
   c. blood reagent chemistry means supported within said housing;
   d. fluid transporting means including said first opening in said housing for transporting a liquid substance flowing from said punctured surface to said reagent means;
   e. at least one opening in said housing for providing a liquid substance to said reagent means; and,
   f. aperture means through said housing adjacent said system positioned to pass light from at least a portion of said reagent means in said diagnostic unit to a sensing means in said system for a determination of color change of said reagent means by the system whereby said color change indicates a diagnostic condition.

2. The disposable diagnostic unit of claim 1 wherein said puncturing means is movable between a retracted position in which said puncturing means is retracted substantially within said housing, and a puncturing position in which said puncturing means extends outwardly from said housing.

3. The disposable diagnostic unit of claim 2 including spring means serving to bias said puncturing means towards said retracted position.

4. The disposable diagnostic unit of claim 1 wherein said puncturing means includes a puncturing point mounted in cantilevered relationship with respect to a portion of said housing.

5. The disposable diagnostic unit of claim 3 wherein said puncturing means includes a puncturing point mounted in a cantilevered relationship with respect to a portion of said housing.

6. The disposable diagnostic unit of claim 5 wherein said puncturing means is spring biased toward said retracted position by said cantilevered relationship.

7. The disposable diagnostic unit of claim 1 wherein said puncturing means includes a puncturing end and an actuation force receiving end.

8. The disposable diagnostic unit of claim 7 wherein said housing includes opposed, substantially parallel first and second upper and lower wall portions.

9. The disposable diagnostic unit of claim 8 wherein said first and second wall portions include first and second openings respectively, each being substantially aligned with said puncturing means, and wherein said first opening is substantially aligned with said puncturing end and said second opening is substantially aligned with said actuation force receiving end.

10. The disposable diagnostic unit of claim 9 wherein said opening for providing a liquid substance to said reagent means includes said first opening.

11. The disposable diagnostic unit of claim 9 including a removable first protective barrier covering said first opening.

12. The disposable diagnostic unit of claim 11 including a second protective barrier covering said second opening.

13. The disposable unit of claim 1 wherein said fluid transporting means includes filter means for filtering at least one component from said liquid substance.

14. The disposable diagnostic unit of claim 3 wherein said spring means positions said puncturing means to travel in an arcuate path.

15. The disposable diagnostic unit of claim 1 including calibration means supported in an aperture in said housing next to said reagent means.

16. The disposable diagnostic unit of claim 1 wherein said fluid transporting means comprises a wicking means.

17. A disposable diagnostic lancet reagent unit for operating in engagement and use with a medical diagnostic system on a type having actuation means for driving of a puncturing means, connection means for operatively receiving said unit on said system and means in said system for reading a color change on the reagent means, said disposable diagnostic lancet reagent unit comprising:
   a. a housing;
   b. means on said housing for operatively connecting said unit to said system;
   c. puncturing means supported within said housing and aligned with a first opening in said housing for allowing said puncturing means to protrude therethrough and to puncture a surface adjacent said housing and cause a flow of liquid substance from said punctured surface when driven by said actuating means;
   d. reagent means, having a front side facing said surface and a back side away from said surface, supported within said housing;
   e. liquid conveying means including said first opening in said housing for conveying said liquid substance from said punctured surface to said reagent means; and,
   f. aperture means through said housing at a point adjacent said system unit for conveying light from a back side portion of said reagent means to said system for determination of color change, thereby indicating a diagnostic condition.

18. The disposable diagnostic unit of claim 17 wherein said liquid conveying means includes means for filtering at least one component of said liquid substance.

19. The disposable diagnostic unit of claim 17 wherein said surface is skin and said liquid substance is blood.

20. The disposable diagnostic unit of claim 17 wherein the color change of said reagent is caused by glucose in said liquid substance and said diagnostic condition is glucose level.

21. The disposable diagnostic unit of claim 17 wherein said fluid conveying means comprises a wicking means between said first opening and said reagent means.

22. A disposable diagnostic lancet reagent unit for operating in engagement and use with a medical diagnostic system of a type having actuation means for driving of a puncturing means, connection means for operatively receiving said reagent unit on said system and means in said system for reading a color change on the reagent means, said disposable diagnostic lancet reagent unit comprising:
   a. a housing including opposing finger gripping taps and a bottom plate;
   b. means on said system housing for operatively connecting said reagent unit to said system;
   c. puncturing means supported within said housing and a first opening in a base of said housing for allowing said puncturing means to protrude therethrough when driven by said actuating means and puncture a surface adjacent said housing and cause a flow of liquid from said puncturing surface;
   d. reagent means, having a variable color responsive to the concentration of a material, supported within said housing;
   e. liquid conveying means including said first opening in said housing for conveying a liquid substance from said punctured surface to said reagent means; and,
   f. aperture means through said housing for providing access for reading said reagent means for change of color by said system thereby indicating a diagnostic condition.

23. The unit of claim 22 wherein said liquid conveying means includes wicking means between said first opening and said aperture.

24. The unit of claim 22 wherein said liquid conveying means includes filter means between said reagent and said wicking means.

25. The unit of claim 22 including a second opening in said housing and a lot/lot calibration positioned about said second opening.

26. The unit of claim 22 including a sterility barrier means adhesively mounted on said bottom plate of said housing member.

* * * * *